(12) United States Patent
Patterson et al.

(10) Patent No.: US 8,221,478 B2
(45) Date of Patent: Jul. 17, 2012

(54) SNAP-OFF SURGICAL SCREW

(75) Inventors: Chad J. Patterson, Bartlett, TN (US); Jeffrey G. Roberts, Germantown, TN (US); Robert M. Fenci, Cordova, TN (US)

(73) Assignee: Wright Medical Technology Inc., Arlington, TN (US)

( * ) Notice: Subject to any disclaimer, the term of this patent is extended or adjusted under 35 U.S.C. 154(b) by 1953 days.

(21) Appl. No.: 11/060,965

(22) Filed: Feb. 18, 2005

(65) Prior Publication Data
US 2006/0081553 A1 Apr. 20, 2006

Related U.S. Application Data

(63) Continuation-in-part of application No. 10/940,396, filed on Sep. 14, 2004.

(51) Int. Cl.
*A61B 17/04* (2006.01)
(52) U.S. Cl. ........................ 606/305; 606/104
(58) Field of Classification Search .......... 606/300–320; 411/2, 39–42, 476
See application file for complete search history.

(56) References Cited

U.S. PATENT DOCUMENTS

| | | | | |
|---|---|---|---|---|
| 4,488,843 A | * | 12/1984 | Achille | 411/41 |
| 5,108,399 A | * | 4/1992 | Eitenmuller et al. | 606/77 |
| 5,971,987 A | * | 10/1999 | Huxel et al. | 606/916 |
| 2003/0158556 A1 | * | 8/2003 | Taras et al. | 606/73 |

FOREIGN PATENT DOCUMENTS

| | | |
|---|---|---|
| EP | 0323429 | 12/1988 |
| EP | 0634811 | 6/1994 |
| FR | 2781998 | 8/1998 |
| FR | 2825015 | 5/2001 |
| WO | WO03/041599 A1 | 5/2003 |
| WO | WO2004/072496 A1 | 8/2004 |

OTHER PUBLICATIONS

International Search Report, PCT International Search Report mailed May 10, 2006 for PCT/US2006/032333 (filed Sep. 9, 2005).

* cited by examiner

*Primary Examiner* — Eduardo C Robert
*Assistant Examiner* — Tara Carter

(57) ABSTRACT

A snap-off surgical screw configured for threading into a bone of a patient using a driver member, comprising a shaft extension joined to a screw portion via a frangible connection. The frangible connection comprises at least one defect formed through an outer surface of the frangible connection. The defect is configured to promote selective separation of the shaft extension from the screw portion at the defect. A proximal end of the screw portion is preferably provided with a recess, and the frangible connection is preferably positioned in the recess to thereby configure the shaft extension to snap-off from the screw portion below the proximal end of the screw portion.

21 Claims, 24 Drawing Sheets

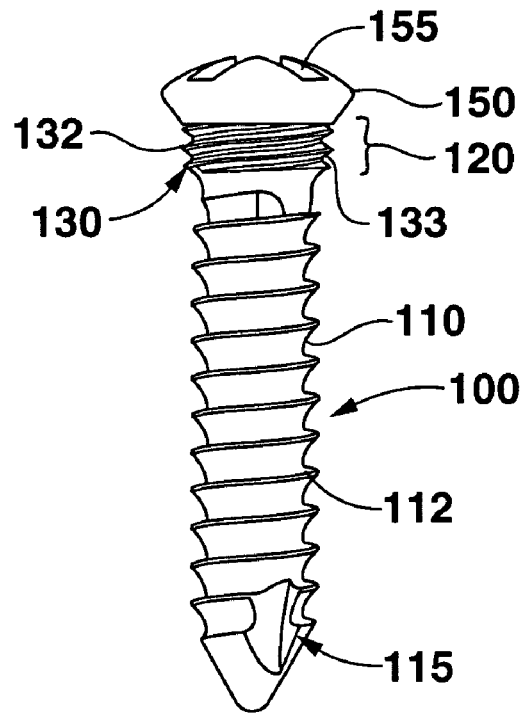
FIG. 11A
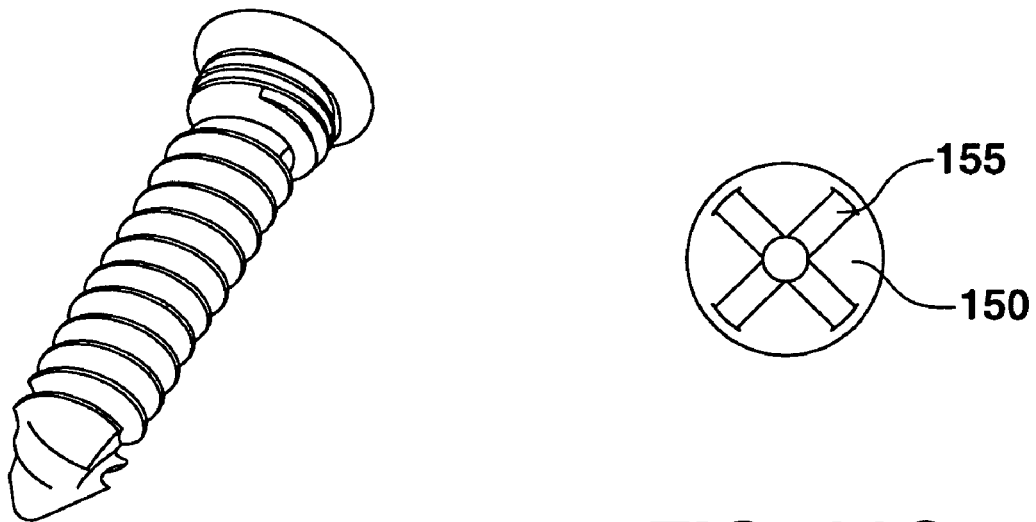
FIG. 11B
FIG. 11C

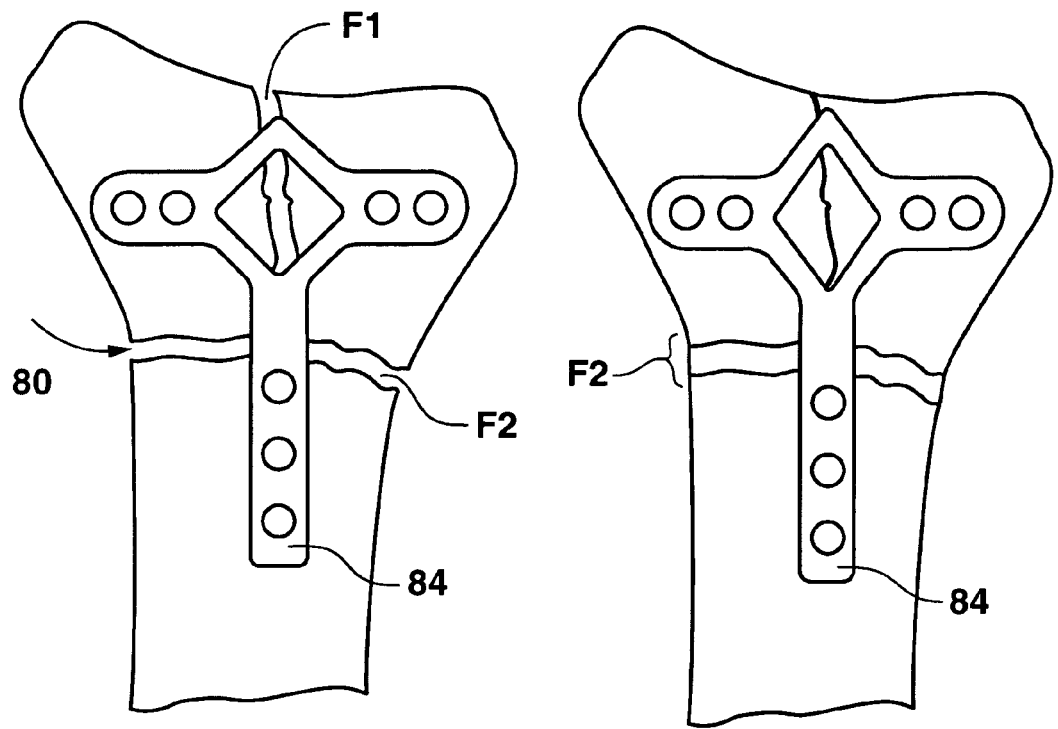
FIG. 25A  FIG. 25B
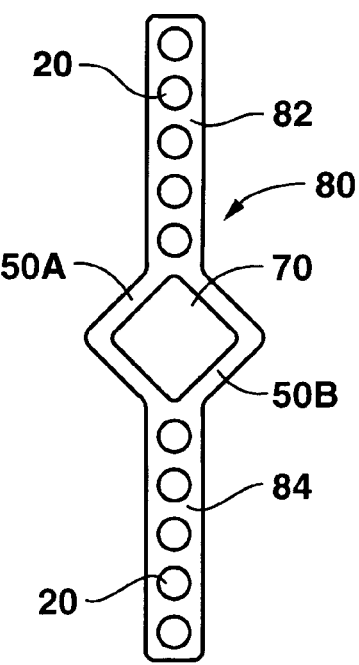
FIG. 26

SNAP-OFF SURGICAL SCREW

CROSS REFERENCE TO RELATED APPLICATIONS

This application is a continuation-in-part of and claims priority to application Ser. No. 10/940,396, filed Sep. 14, 2004, which is pending.

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to surgical screws, and more particularly to surgical screws having a breakaway head.

BACKGROUND OF THE INVENTION

Breakaway surgical screws are known in the art. See e.g. U.S. Pat. No. 6,723,099 (Goshert), which is incorporated herein by reference. A breakaway surgical screw has a proximal head and a distal shaft or shank in the manner of a conventional screw, and additionally has a driver portion extending proximally from the head. The driver portion is configured for engagement by a drill chuck. The drill is used to rotate the screw and thus drive the screw into bone. Once the screw is in place, the driver portion can be broken off of the head of the screw.

One problem encountered with prior art breakaway surgical screws is inconsistency in the breakaway zone. After the driver portion has been removed, fragments of the driver portion often remain on the head of the screw, where they can irritate tissues of the patient.

There is thus a need for a snap-off surgical screw having the following characteristics and advantages over the prior art.

OBJECTS AND SUMMARY OF THE INVENTION

It is an object of the invention to provide a snap-off surgical screw that is configured to break apart at a selected point to provide a residual screw without substantial remnants of a frangible region.

The foregoing and other objects are met by providing a snap-off surgical screw comprising a shaft extension joined to a screw portion via a frangible connection, the frangible connection comprising at least one defect formed through an outer surface of the frangible connection. The defect is configured to promote selective separation of the shaft extension from the screw portion at the defect. A proximal end of the screw portion is preferably provided with a recess, and the frangible connection is preferably positioned in the recess to thereby configure the shaft extension to snap-off from the screw portion below the proximal end of the screw portion. A driver engaging portion of the shaft extension may comprise an enlarged portion of the shaft extension, the enlarged portion adjacent and proximal to a proximal end of the screw portion, and the enlarged portion including a plurality of slots therein, the slots configured for engagement by a driver member. The driver engaging portion may include a quick connect means for quickly connecting the screw to a quick connect coupling member. The driver engaging portion preferably includes a non-circumferential portion configured to engage the driver member in a non-rotational relationship.

The foregoing and other objects, features, aspects and advantages of the invention will become more apparent from the following detailed description of the invention when considered in conjunction with the accompanying drawings.

BRIEF DESCRIPTION OF THE DRAWINGS

FIG. 11 is a side view of a preferred embodiment of a screw type fastener for use in the invention.

FIGS. 25A-25B show the use of a fracture fixation plate to reduce a fracture of the radius.

FIG. 26 shows a top view of one preferred embodiment of a fracture fixation plate having a compression opening.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

The present application is directed primarily to the invention that shown in FIGS. 22A-22G and which is discussed in further detail below.

Figure 4:
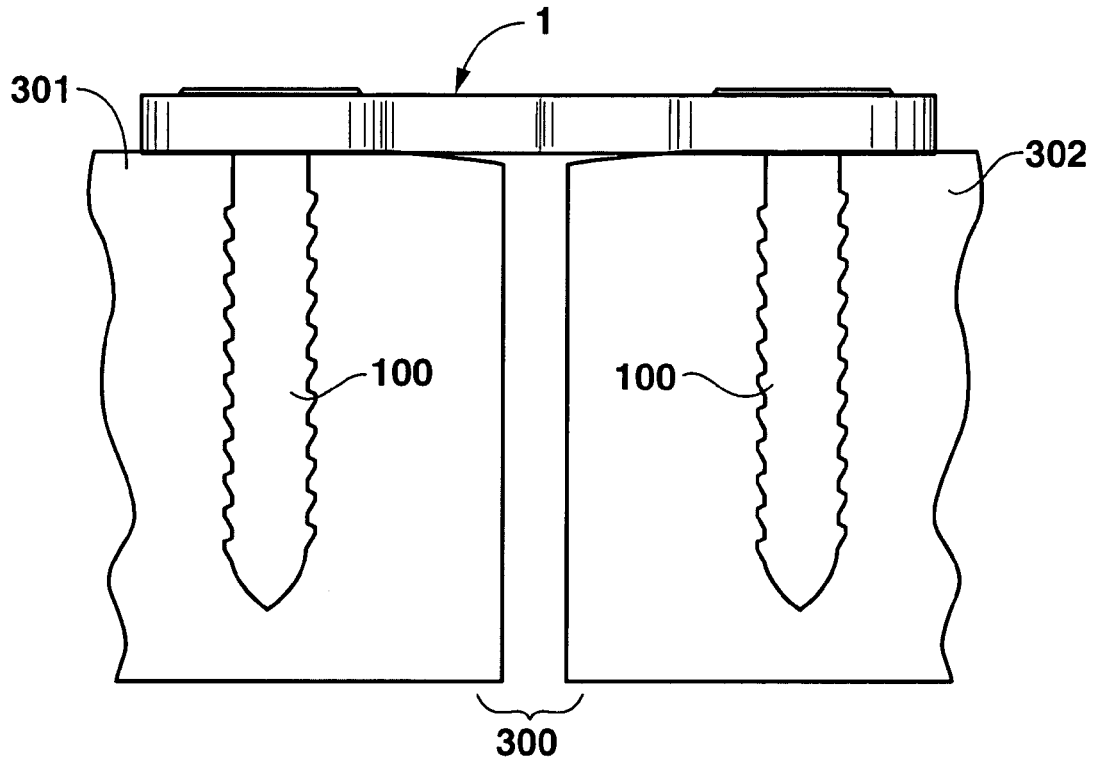
FIG. 4 is a side partial cross-section view illustrating use of the compression brace of the invention to reduce a fracture by drawing adjacent bones together, featuring the brace in an uncompressed configuration prior to reduction of the fracture.
Figure 5:
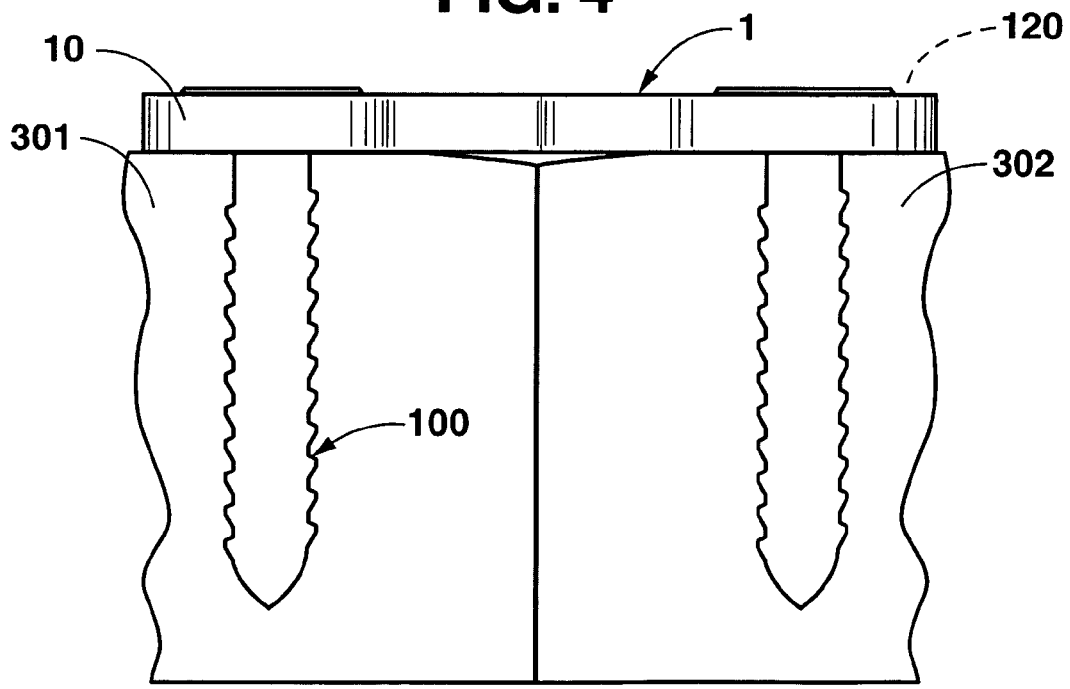
FIG. 5 is a side partial cross-section view illustrating use of the compression brace of the invention to reduce a fracture by drawing adjacent bones together, featuring the brace in a compressed configuration.

As shown in FIGS. 4 and 5, the invention is a surgical device for pressing and retaining adjacent bones 301, 302 against one another, such as to reduce a fracture. As shown in the uncompressed configuration of FIG. 4, the invention includes, generally, a compression brace 1 and fasteners 100 for securing the brace on bones 301, 302. As indicated in the compressed configuration of FIG. 5, compression of the brace 1 presses the adjacent bone fragments 301, 302 together.

Figure 1:
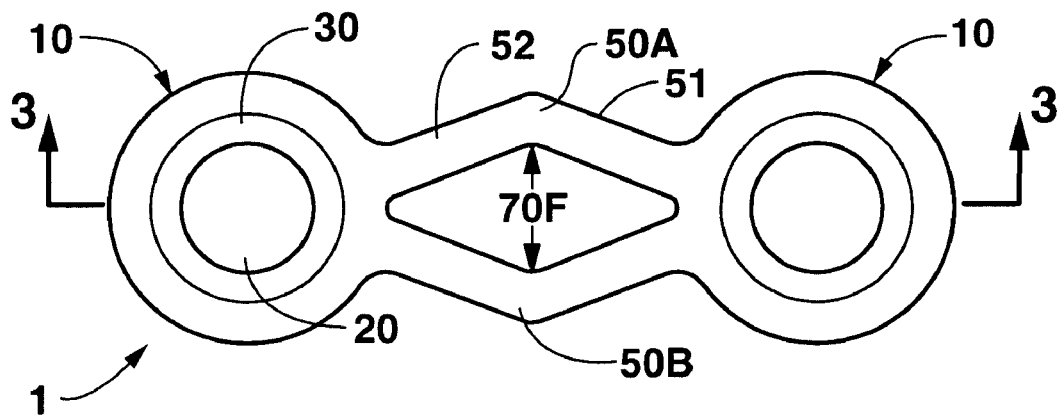
FIG. 1 is a top view of one preferred embodiment of a compression brace of the invention, showing the brace in an uncompressed configuration.
Figure 3:
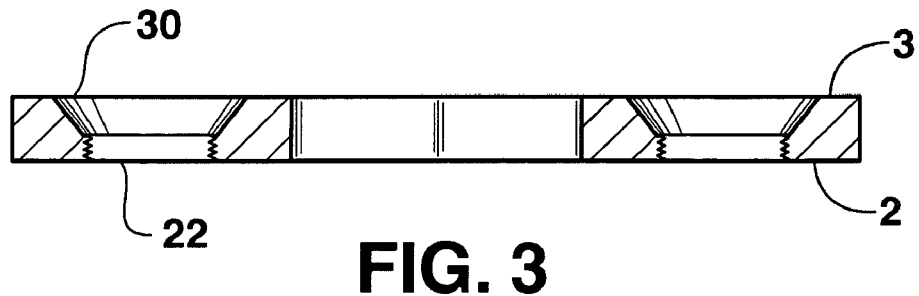
FIG. 3 is a side cross-section of view taken along 3-3 of FIG. 1.

As shown in FIG. 1, in a preferred embodiment the compression brace 1 has at least two fastener retaining portions 10. Each fastener retaining portion 10 has a fastener hole or bore 20 therethrough for receiving a fastener 100. In a preferred embodiment shown in FIG. 3, a thread 22 is provided in the fastener hole 20. As indicated in the side view of FIG. 3, the brace 1 can be considered to have a tissue or osteo side 2, which sits against the bones during use, and an opposing side or outer surface 3. As shown in FIG. 3, the fastener retaining portion 10 preferably has a counterbore 30 formed in the outer surface 3. The counterbore 30 is preferably substantially in axial alignment with the fastener hole 20. The counterbore 30 is preferably spherical. The counterbore 30 is sized and configured to provide countersinking of an upper retainer portion 150 of a fastener 100 in the fastener retaining portion 10 of the compression brace 1.

A pair of bridge members 50A, 50B are positioned between the fastener retaining portions 10. The bridge members 50A, 50B preferably extend directly from the fastener retaining portions 10, but may be spaced from one or both of the fastener retaining portions, such as by a shared extension portion disposed between the bridge members 50A, 50B and fastener retainer portions 10. The bridge members 50A, 50B are spaced apart from one another to form a compression opening 70 between the fastener retaining portions 10. The bridge members 50A, 50B and the compression opening 70 are used to compress the fastener retaining portions 10 and fasteners 100 toward one another, in a manner described in further detail below.

Figure 2:
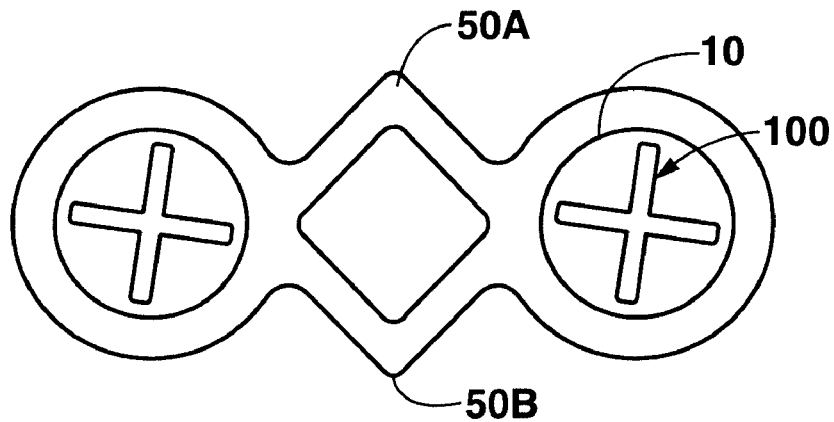
FIG. 2 is a top view of the compression brace of FIG. 1, showing the brace in a compressed configuration and featuring a pair of screws disposed in the brace.

In the preferred embodiment shown in FIG. 1, the bridge members 50A, 50B are substantially V-shaped. The V-shape is preferably formed by generally linear portions 51, 52, which normally join one another at an obtuse angle when the brace 10 is in an uncompressed configuration. When opposing expansion forces are applied to the bridges 50A, 50B substantially along lines of force F in FIG. 1, central portions of the bridge members 50A, 50B expand outward, thus drawing or compressing the fastener retaining portions 10 toward one another. FIG. 2 demonstrates the configuration of the compression brace of FIG. 1 after it has been compressed a selected amount. Note that in FIG. 2, the compression brace 1 has contracted generally along its lengthwise axis, while the opposing bridge members 50A, 50B have expanded in directions generally transverse to the lengthwise axis. Alternatively, the bridge members 50A, 50B can be pinched toward one another. Pinching will tend to force the fastener retaining portions 10 apart, particularly when using a V-shaped opening, which can be useful for certain surgical applications, such as distractions. In this manner, the compression brace 1 can be used both for compression and distraction, as well as to provide for fine-tuning of bone gap sizes and compressive forces. Pinching can also be used to force the fastener retaining portions 10 toward one another, resulting in compression.

Figure 6:
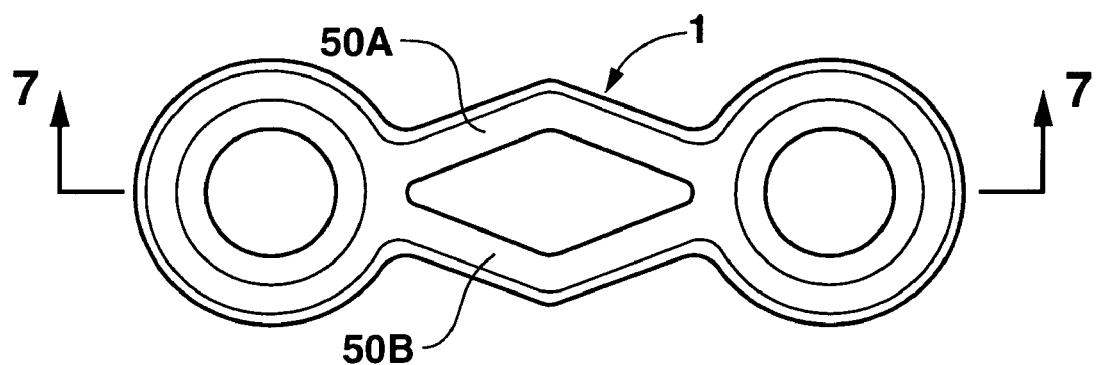
FIG. 6 is a top view of a preferred embodiment of the compression brace of the invention, featuring an unthreaded fastener hole.

Bridge members 50A, 50B may alternatively have curved, arcuate, straight, or other deformable configurations, provided that bridges 50A, 50B are configured to form a deformable compression opening 70. In FIG. 6, the bridge members 50A, 50B are shortened and form a tighter angle along the compression opening 70. FIG. 6 also shows an embodiment in which a chamfer is formed along the upper edge of the compression brace 1.

As shown in FIG. 4, fasteners 100 are used to secure the bracket 1 to adjacent bones 301, 302. Each fastener 100 is sized and configured to pass through a fastener hole 20 and to retain the compression bracket 1 on bones 301, 302. Fasteners 100 of differing diameter can be used. For example, if angulation of the fastener 100 is desired, a smaller diameter may be used. The fasteners 100 may be locking or non-locking. In a preferred embodiment shown in FIG. 11, each fastener 100 has a lengthwise shaft 110 sized to pass through at least one of the fastener holes 20, and an upper retainer portion 150 sized and configured to retain the fastener 100 in the fastener hole 20. As shown in FIG. 11, the retainer portion 150 is preferably a circumferential head of the type used in conventional screws. The head 150 is preferably provided with a self-retaining drive mechanism, such as press-fit drive slots 155.

As shown in FIG. 11, the fastener 100 is preferably a screw 100, in which case the shaft 110 is provided with a lower thread 112 that is positioned to engage bone. The lower thread 112 is preferably self-tapping and self-drilling in bone. To facilitate tapping of the lower thread 112 into bone, a cutting means 115 is preferably provided on or adjacent the tip of the screw 100. Cutting means are well known to those of skill in the art of surgical screws.

Figure 12A:
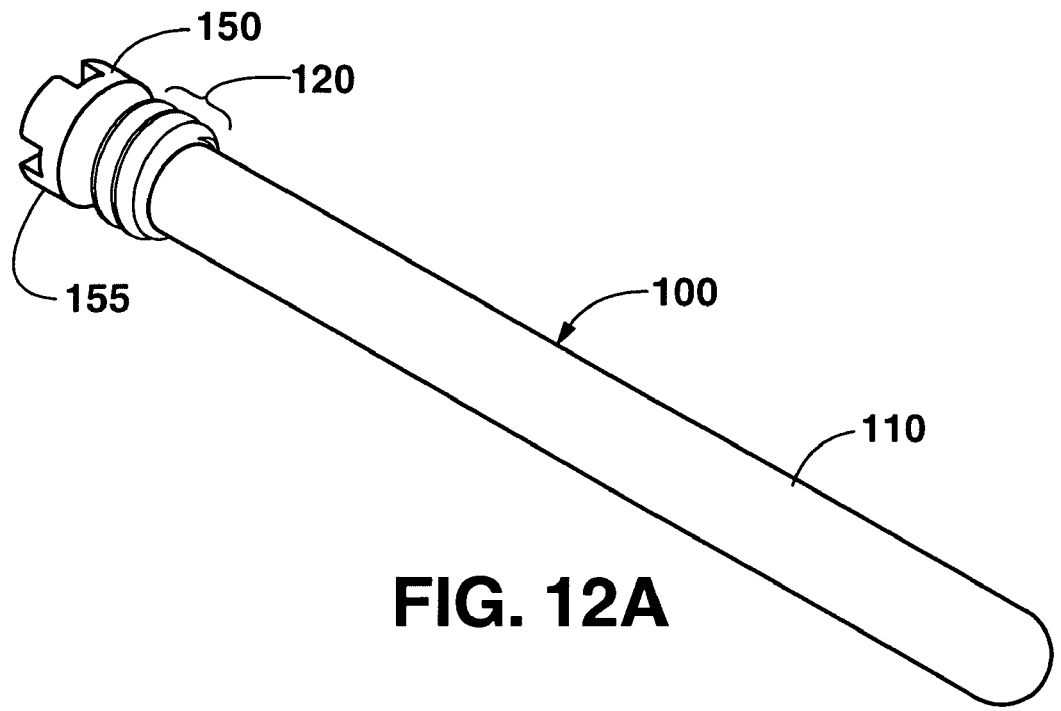
FIG. 12 is a side perspective view of a preferred embodiment of a pin-type fastener for use in the invention.
Figure 12B:
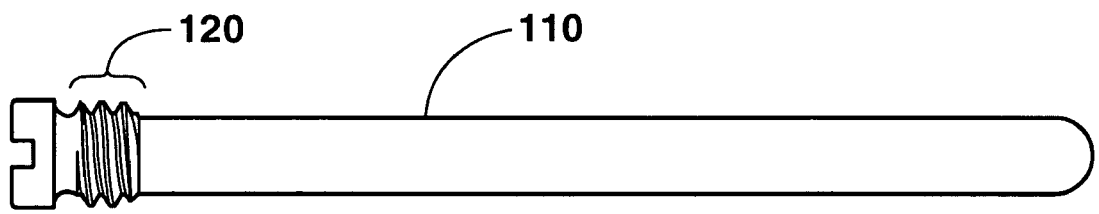
Figure 12C:
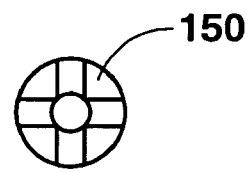
Figure 13A:
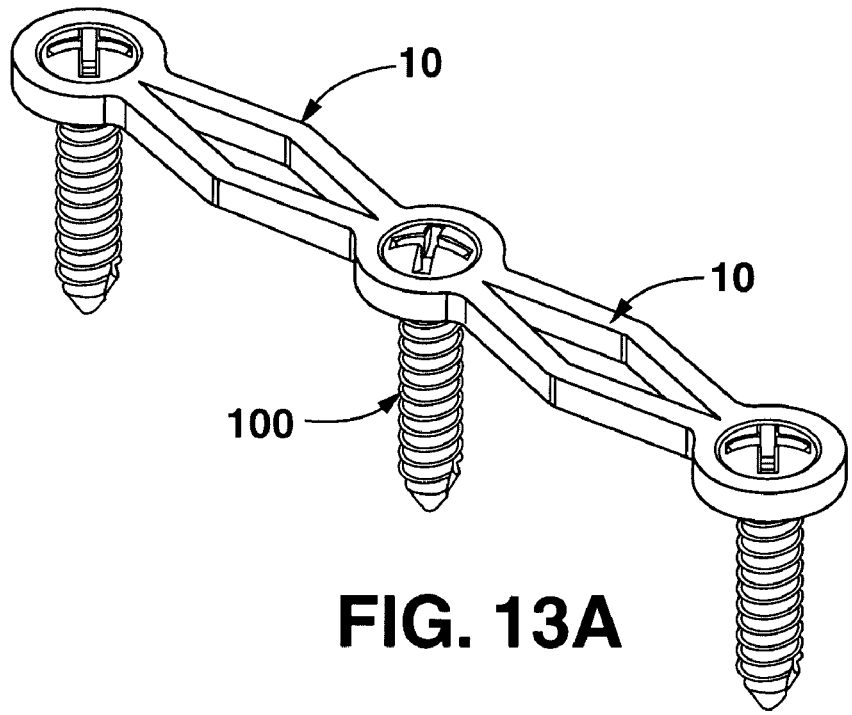
FIG. 13 provides views of one preferred embodiment of the invention, featuring a pair of compression brackets joined end-to-end via a shared fastener retaining portion.
Figure 13B:
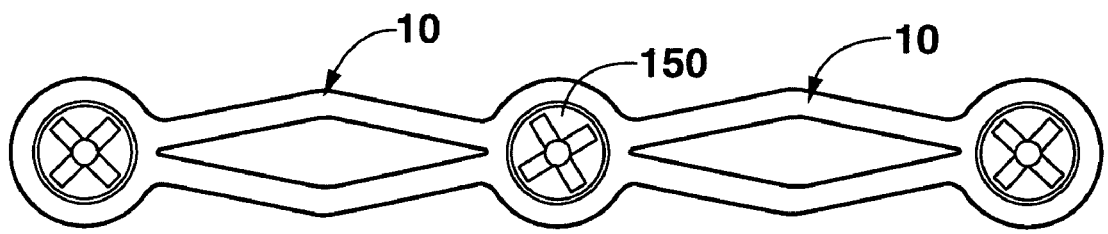
Figure 13C:
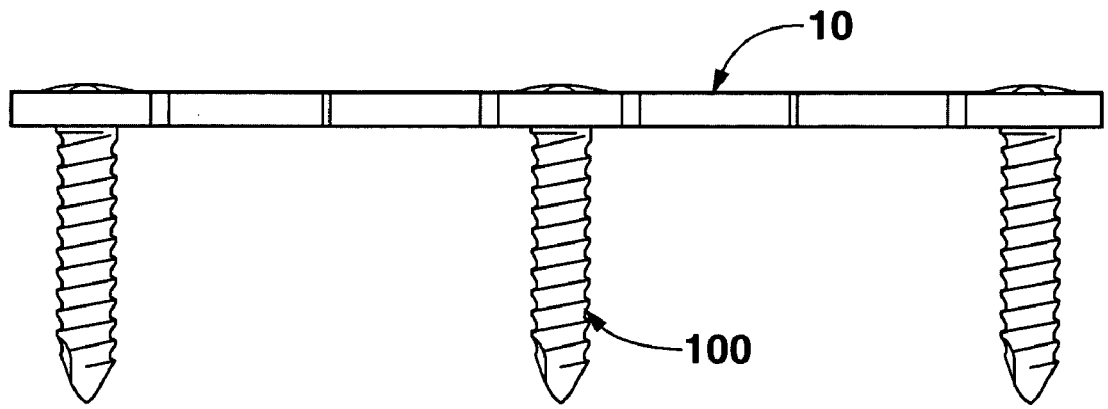
Figure 14A:
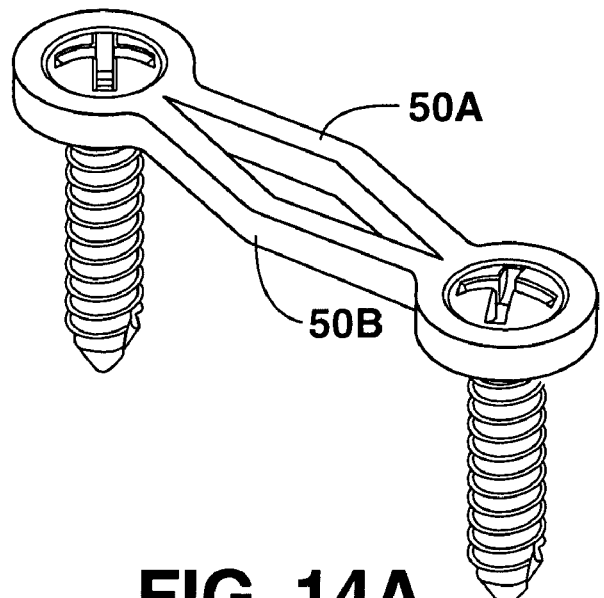
FIG. 14 provides views of one preferred embodiment of the invention.
Figure 14B:
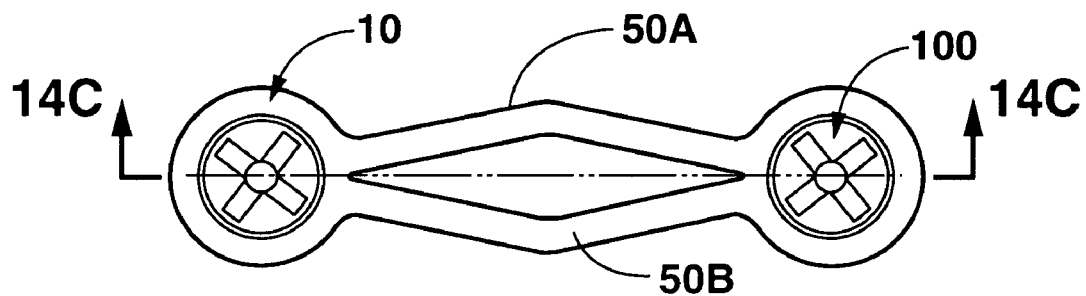
Figure 14C:
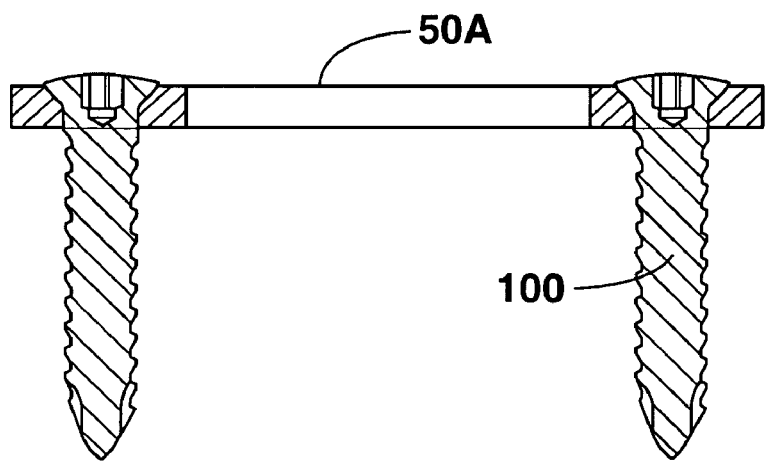
Figure 15A:
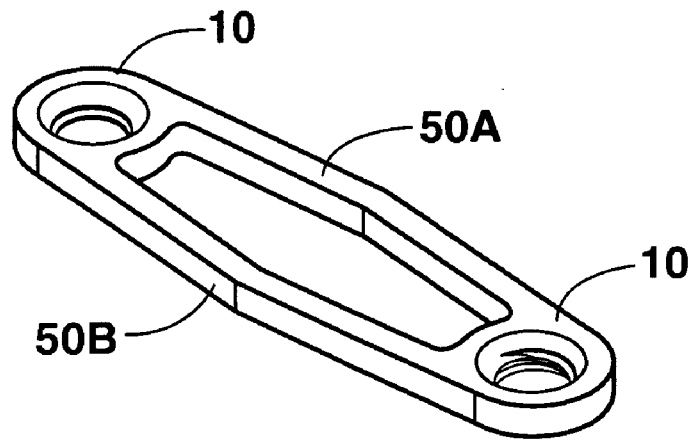
FIG. 15 provides views of one preferred embodiment of the invention.
Figure 15B:
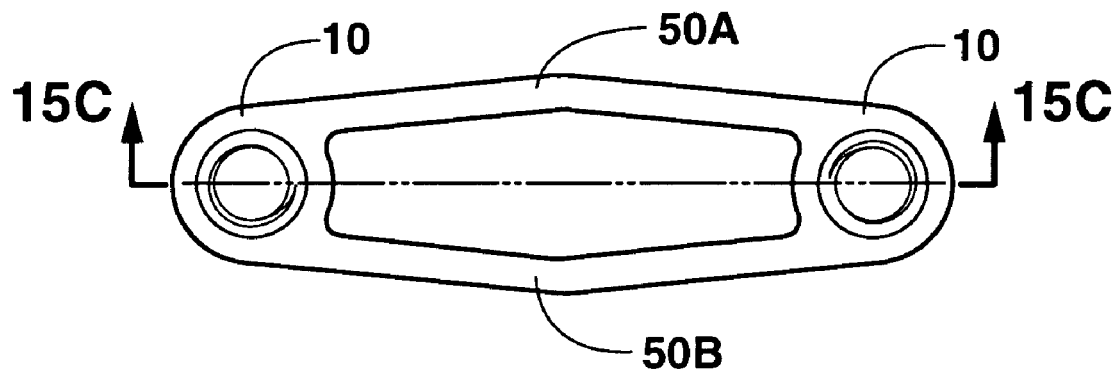
Figure 15C:
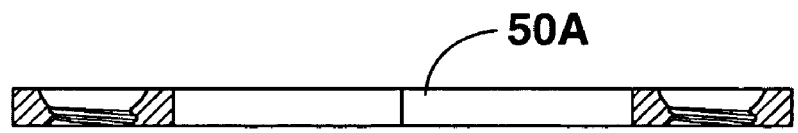

As shown in FIG. 12, an alternative preferred fastener 100 is a pin 100. The pin 100 shown in FIG. 12 has an enlarged head or fastener retainer portion 150 configured to retain the pin 100 in the fastener retainer member 10. The shaft 110 of the pin 100 preferably has a substantially smooth outer surface.

In a preferred embodiment shown in FIG. 11, an upper thread 120 is provided on the shaft 110 adjacent the head of the fastener 100 for use in engaging the internal thread 22 in the fastener hole 20. In a preferred embodiment, the upper thread 120 of the fastener 100 and the internal thread 22 of the compression brace 1 serve to maintain the fastener 100 in a substantially fixed relation to the fastener retaining portion 10. For example, in FIG. 5, an upper thread 120 has maintained the fasteners 100 in a substantially perpendicular relation to the fastener retainer portion 10. In the preferred embodiment of FIG. 5, the fasteners 100 have maintained a substantially fixed relation even after the compression bracket 1 has been compressed to draw the bones 301, 302 together. A substantially fixed relationship can also be obtained by providing a snug-fit screw head appropriately sized to the fastener hole 20 and counterbore 30. In the prior art uni-body compression staples disclosed in the Groiso patents, the pins of the staples tend to splay outward significantly during use in vivo, decreasing the compressive strength of the staples.

The invention may be provided with a means 130 for selectively locking the fastener 100 in the fastener hole 20. In the preferred embodiment shown in FIG. 11, the locking means 130 is provided by forming the upper thread 120 from double-lead threads 132, 133. The double-lead threads 132, 133 provide selective locking of the fastener 100 in the fastener hole 20 via locking interaction with the single internal thread 22 of the fastener hole 20. One advantage of a double-lead type of locking means 130 is that the threads can be configured such that the compression bracket 1 can be reused, for example if it becomes necessary to remove and replace or reposition the original fastener 100. Other locking means include mismatched threads.

Figure 7:
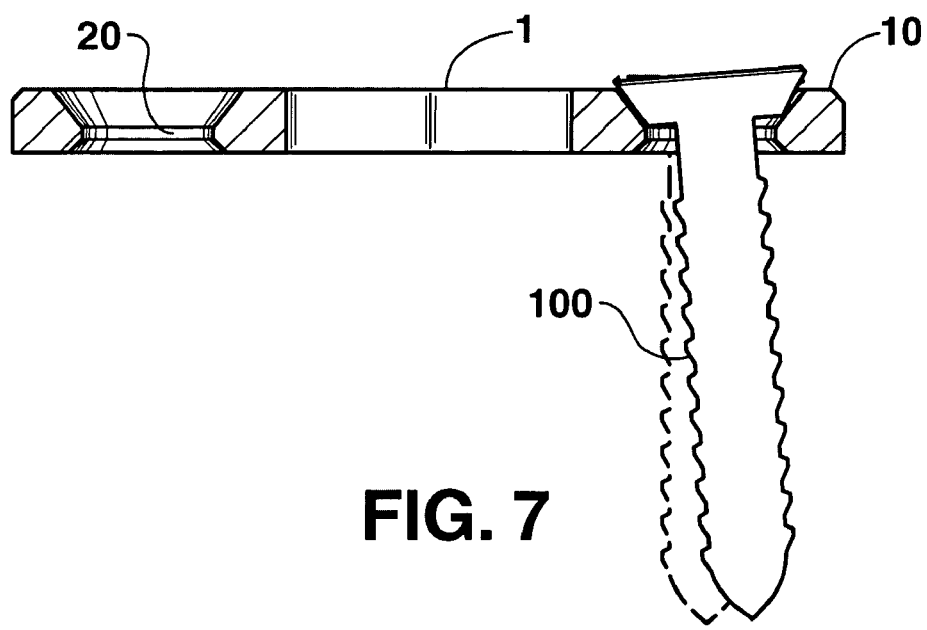
FIG. 7 is a side cross-section view taken along 7-7 of FIG. 6, and illustrating radial play of a screw within the unthreaded fastener hole.

As shown in FIG. 7, the surgical device may be configured such that there is play between the fastener 100 and the fastener retaining portion 10. In the preferred embodiment shown in FIG. 7, the fastener hole 20 of the brace member is substantially smooth, i.e. unthreaded. Additionally, the shaft 110 of the fastener 100 is sized to provide play between the shaft 100 and the fastener hole 20. As indicated in FIG. 7, this configuration allows the fastener 100 to be selectively angled into bone during use of the device.

Snap-off screws, such as the type shown in FIG. 22, can be used as fasteners 100. The snap-off surgical screw shown in FIG. 22B is similar to the screws described above in that it has a head 150, an upper threaded part 120 providing a locking thread 130 distal to the head, and a bore thread 112 distal to the locking thread 130. Additionally, a shaft extension 160 extends above the poly-axial head for use in rotating and driving the screw. The shaft extension 160 is axially aligned with the screw 100. A distal end of the shaft extension 160 is fixedly connected to the head 150 of the screw by a narrow shaft 161. After the screw 100 is inserted, the shaft 160 is broken off of the screw 100 at the point of the narrow shaft 161.

Figure 22A:
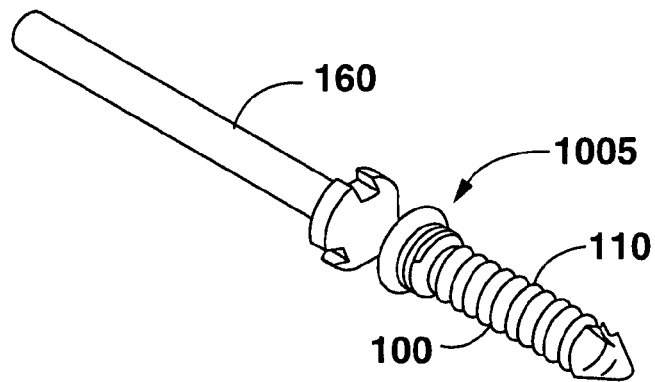
FIG. 22A is a side perspective view of one preferred embodiment of the snap-off surgical screw of the invention.
Figure 22B:
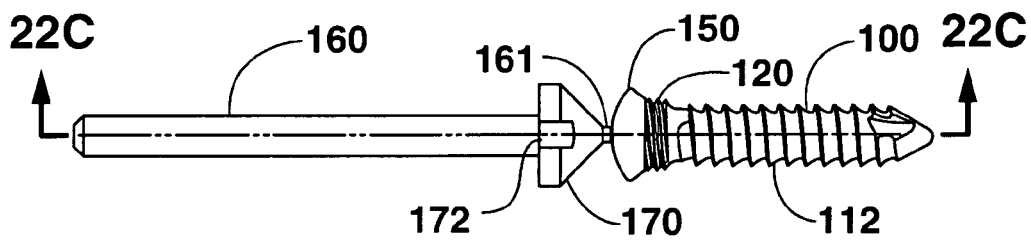
FIG. 22B is a side view of one preferred embodiment of the snap-off surgical screw of the invention.
Figure 22C:
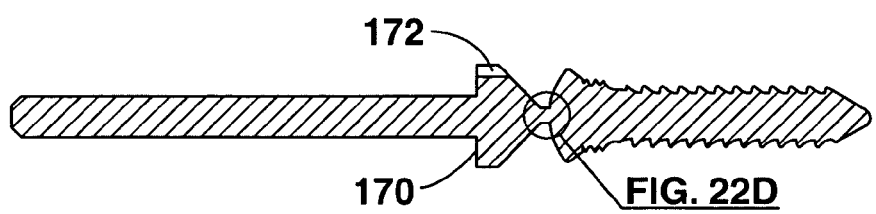
FIG. 22C is a cross-section view taken along B-B of FIG. 22B.

With reference to FIGS. 22A-22G, the present application is directed toward embodiments of a snap-off surgical screw 100, the basic features of which are described in applicant's U.S. patent application Ser. No. 10/940,396, which is incorporated herein by reference. As discussed in Ser. No. 10/940,396, snap-off screws 100S, such as the type shown in FIG. 22, can be used as fasteners 100. The snap-off surgical screw shown in FIG. 22B is similar to the screws described above in that it has a head 150, an upper threaded part 120 providing a locking thread 130 distal to the head, and a bore thread 112 distal to the locking thread 130. Additionally, a shaft extension 160 extends above the poly-axial head for use in rotating and driving the screw 100. The shaft extension 160 is axially aligned with the screw 100. A distal end of the shaft extension 160 is fixedly connected to the head 150 of the screw by a narrow shaft 161. After the screw 100 is inserted, the shaft 160 is broken off of the screw 100 at the point of the narrow shaft 161. The foregoing and additional features of preferred embodiments of snap-off screws 100S will now be described in further detail.

In general, the snap-off surgical screw 100S is configured for threading into a bone of a patient using a conventional driver or a powered driver, such as a drill or reamer. At least a portion of the shaft extension 160 serves as a driver engaging member or portion 170. The driver engaging portion 170 is configured for engagement by a chuck of a conventional drill, such as a Jacobs chuck, or by a quick connect coupling member 177 (discussed below). As will be discussed in further detail below, the driver engaging portion 170 can take various configurations, depending on the type of drill chuck or quick connect coupling member 177 that will be used to engage the driver engaging portion 170.

The driver engaging portion 170 is joined to the screw portion 100 via a frangible connection 161. The frangible connection 161 comprises at least one defect 162 formed through an outer surface of the frangible connection 161. The defect 162 is configured to promote selective separation of the driver engaging portion 170 from the screw portion at the defect 162. The defect 162 can take various forms, such as a circumferential groove or undercut that is narrower than the shaft extension 160, a wedge shaped defect, or a plurality of wedge shaped defects spaced circumferentially around the frangible connection 161. The defect 162 can be a laser mark etched into the frangible connection 161. The defect 162 makes it less likely that fragments of the shaft extension 160 will remain on the screw portion 100 after the shaft extension 160 has been snapped off. The frangible connection 161 can be configured such that it breaks at a selected torque or within a selected torque range. The preferred torque break range is about 2 to about 30 N cm based on a thread size of about 1.0 to about 5.0 mm (major diameter).

Figure 22D:
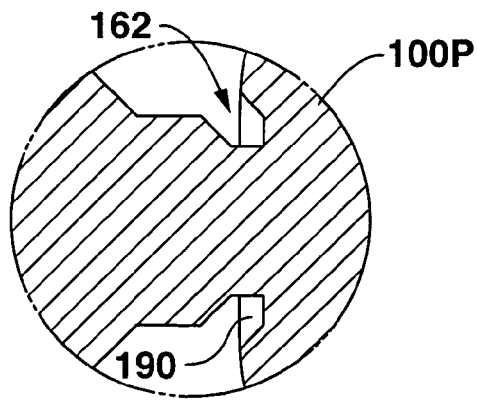
FIG. 22D is a cross-section view featuring details of one preferred embodiment of a frangible connection of the snap-off surgical screw of the invention.

In the preferred embodiment shown in FIG. 22D, a proximal end 100P of the screw portion has a recess 190 therein. The frangible connection 162 is positioned in the recess 190 to thereby configure the shaft extension 160 to snap-off from the screw portion within the recess and below the proximal end 100P of the screw portion 100. The recess 190 thus helps ensure that any fragments of the shaft extension 160 that may remain on the screw portion 100 after the shaft extension 160 has been snapped off will lie below the proximal end 100P of the screw portion 100, where the fragments are less likely to irritate soft tissue.

The lengthwise shaft 110 of the snap-off screw 100S can be provided with various types and combinations of threads and thread features, such as a self-drilling thread or a self-tapping tip.

Figure 22E:
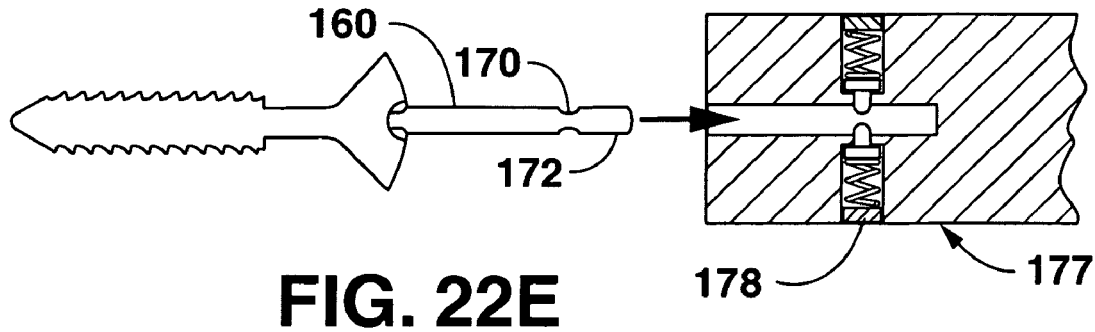
FIG. 22E is a side view of one preferred embodiment of a snap-off screw of the invention, featuring a cross-section view of a quick connect coupling member.

The driver engaging portion 170 of the shaft extension 160 can be provided with various means for providing a connection between the snap-off screw 100S and a driver, such as drill or reamer. Conventional breakaway screws rely on a conventional chuck, such as a Jacobs chuck, to attach the screw to a driver. The connection process can be time consuming, particularly when it is necessary to install multiple breakaway screws. As indicated in FIG. 22E, one aspect of the invention is a quick connect coupling member 177. The quick connect coupling member 177 is configured for connection to the chuck of a driver, such as by a Jacobs chuck. The quick connect coupling 177 includes engagement features 178 that allow the quick connect coupling to quick-connect to the driver engaging portion 170. As indicated in FIG. 22E, the driver engaging portion 170 of the shaft extension 160 in turn includes features that enable the snap-off screw 100S to quick connect to the quick connect coupling 177. The use of a quick connect coupling member 177 and matching quick connect features 172 on the driver engaging portion 170 eliminates the need to use a chuck to connect each screw 100S to a driver. This feature of the invention is particularly beneficial when using multiple snap-off screws 100S in a single procedure.

In the embodiment shown in FIG. 22E, the driver engaging portion 170 of the shaft extension 160 includes a pair of indents or apertures 172 that are spaced to engage ball detents 178 in a quick connect coupling member 177. The matching quick connect coupling member 177 includes spring biased ball detents 178 positioned in a bore. When the shaft extension 160 slides a sufficient distance into the bore of the quick connect coupling member 177, the plungers of the ball detents 178 engage the apertures 172 of the driver engaging portion 170 in a releasable quick-connection.

Figure 22F:
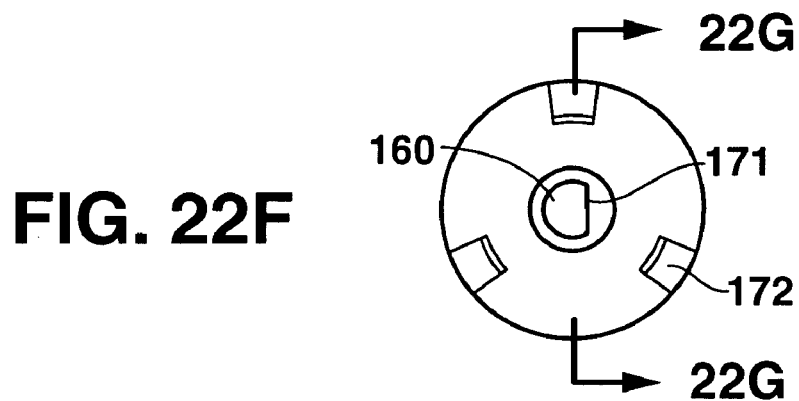
FIG. 22F is a top view of a one preferred embodiment of a snap-off screw of the invention, featuring quick connect coupling features.
Figure 22G:
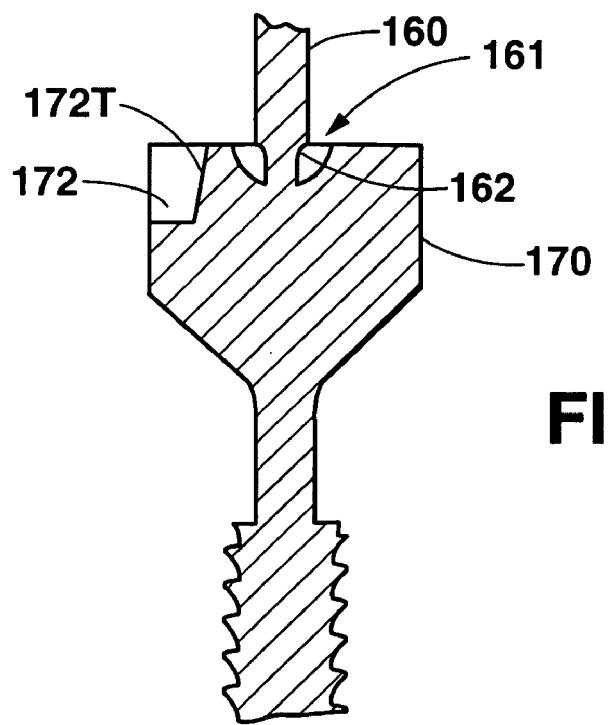
FIG. 22G is a cross-section view taken along A-A of FIG. 22F.

In the embodiment shown in FIGS. 22F-22G, the driver engaging portion 170 of the shaft extension 160 is an enlarged driver head 170. The enlarged driver head 170 is provided with a plurality of slots 172 for receiving matching prongs 178. The prongs 178 could be on a screw driver or on a quick connect coupling member 177. In a preferred embodiment, the enlarged driver head 170 includes three substantially equidistant slots 172 in order to provide a 3-point driving mechanism. The 3-point driving mechanism provides a positive fit with the screw 100S to ensure that the screw stays concentric with the driver during insertion. The driver engaging portion 170 also preferably includes a non-circumferential portion, such as a flat 171, which serves to orient the slots 172 for engagement by the quick connect coupling member 177 as well as to maintain the shaft extension 160 and the driver in a fixed, non-rotating relationship. As shown in the side view cross-section of FIG. 22G, the slots 172 preferably include at least one tapered wall 172T, to assist in seating the quick coupling member 177. Prior art couplings do not employ a tapered wall, and consequently must provide a degree of clearance between the driver tabs and the slots, which results in a looser fit. With a tapered slot 172T and tapered driver, the driver and slot 172 wedge together, resulting in a better fit. An enlarged driver head 170 having slots 172 can also be provided as the head 150 of the screw portion 100.

Figure 16A:
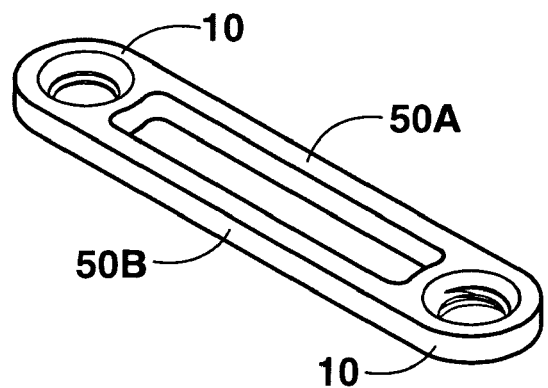
FIG. 16 provides views of one preferred embodiment of the invention.
Figure 16B:
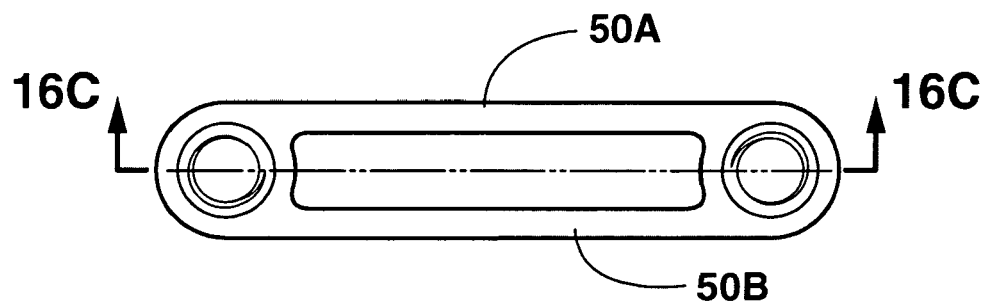
Figure 16C:
Figure 17A:
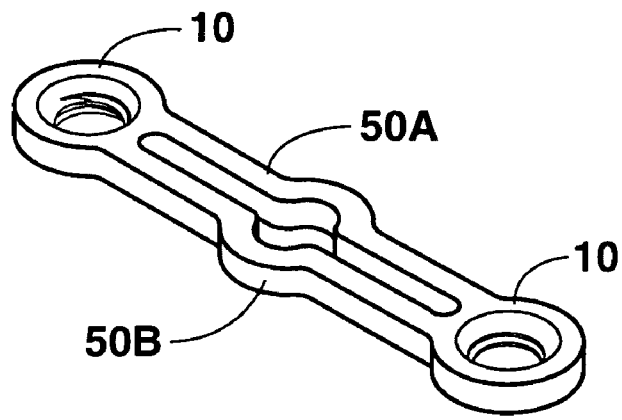
FIG. 17 provides views of one preferred embodiment of the invention.
Figure 17B:
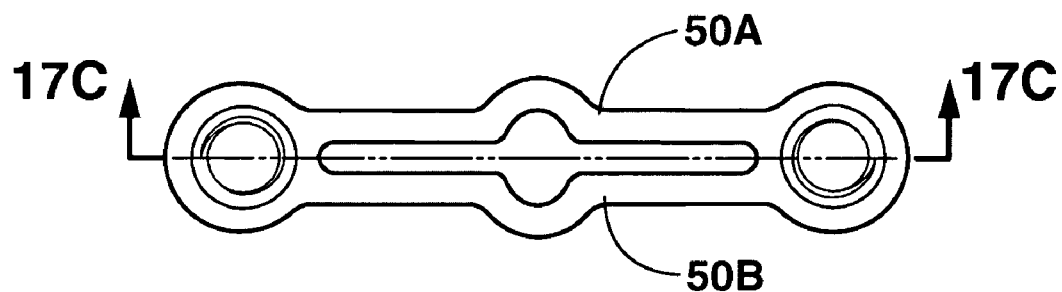
Figure 17C:
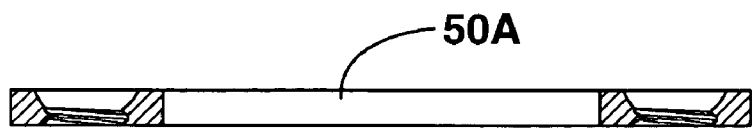

FIGS. 14-17 provide views of various embodiments of compression brackets 1 of the invention. The bracket shown in FIGS. 14A-14C has an elongated compression opening 70. FIGS. 15A-15C show a compression bracket 1 having a spaced apart bridge members 50A, 50B, such that the opposing ends of the bridge members 50A, 50B are not directly adjacent one another. FIGS. 16A-16C show a compression bracket 1 having spaced apart bridge members 50A, 50B. Additionally, the spaced apart bridge members 50A, 50B of FIG. 16 are straight, and thus lack the V-shaped configuration of other embodiments. The configuration of FIG. 16 is particularly adapted for situations in which it may be desirable to obtain compression by bending the bridge members 50A, 50B toward one another rather than by spreading the bridge members apart, although the bridges 50A, 50B can also be spread. The bracket shown in FIGS. 17A-17C has a straight and generally narrow compression opening 70, but is provided with diametrically opposed distal curved portions for use in engaging the bridge members 50A, 50B during spreading of the compression opening 70.

Figure 18A:
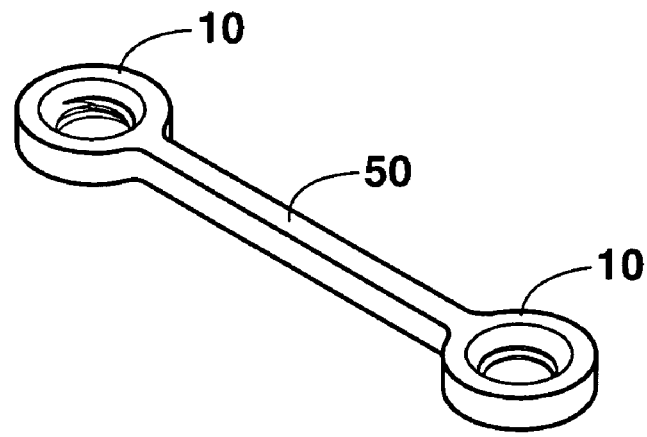
FIG. 18 provides views of one preferred embodiment of the invention.
Figure 18B:
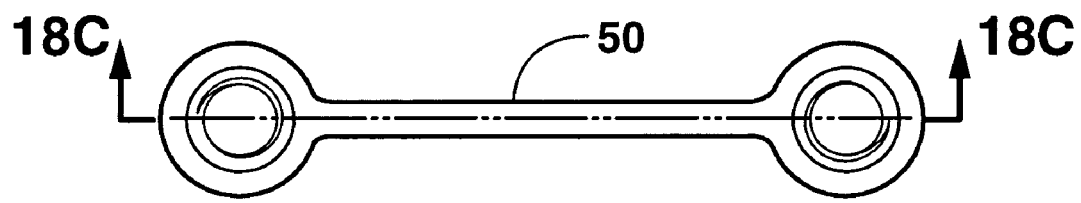
Figure 18C:
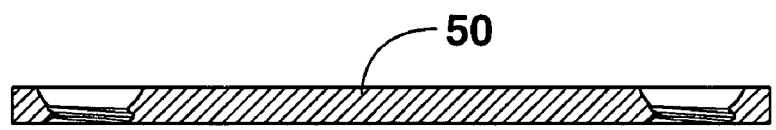

FIGS. 18A-18C show yet another embodiment in which the opposing bridge, and hence the compression opening 70, are eliminated in favor of a single bridge 50. The single bridge 50 can be bent in order to draw the opposing fastener retaining portions 10 together. Otherwise, the embodiment shown in FIGS. 18A-18C can be provided with the various threaded and unthreaded variations described above.

Figure 19A:
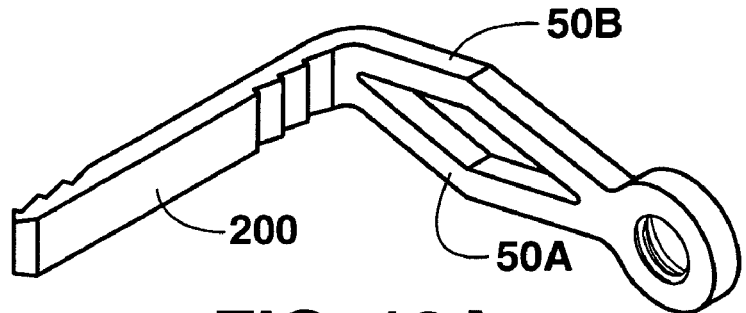
FIG. 19 provides views of one preferred embodiment of the invention.
Figure 19B:
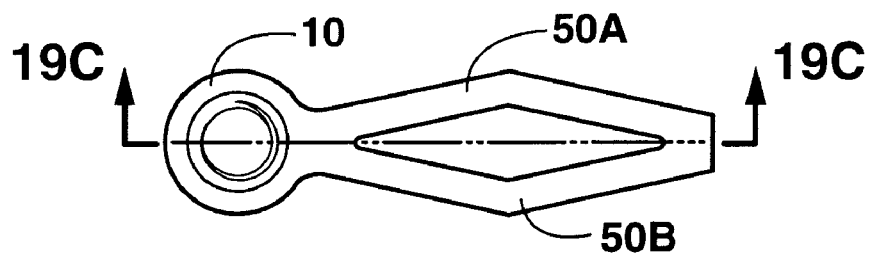
Figure 19C:
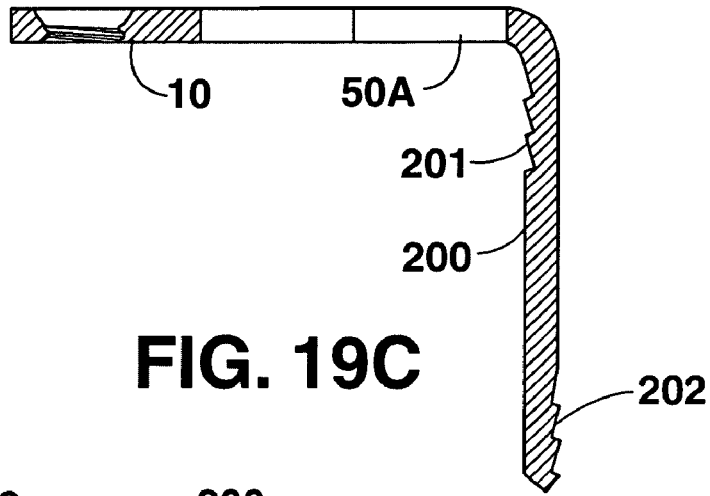
Figure 19D:
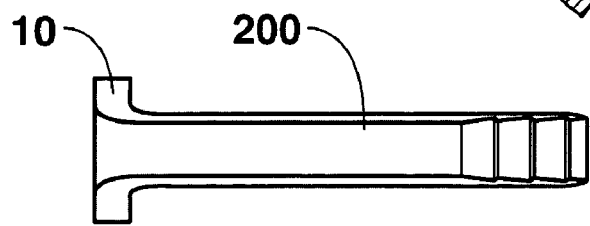

FIGS. 19A-19D show an embodiment that combines the features of prior art surgical staples with the advantages provided by the compression bracket 1 of the present invention. As shown in FIG. 19A, the combined staple-compression bracket includes opposing bridge members 50A, 50B and a fastener retaining portion 10 having the configuration and characteristics described above. However, the opposing end of the device is provided with a downwardly depending leg 200. The downwardly depending leg 200 is preferably provided with means for securing the leg 200 in bone, such as the proximal 201 and distal 202 teeth or serrations shown in FIG. 19C.

Figure 8A:
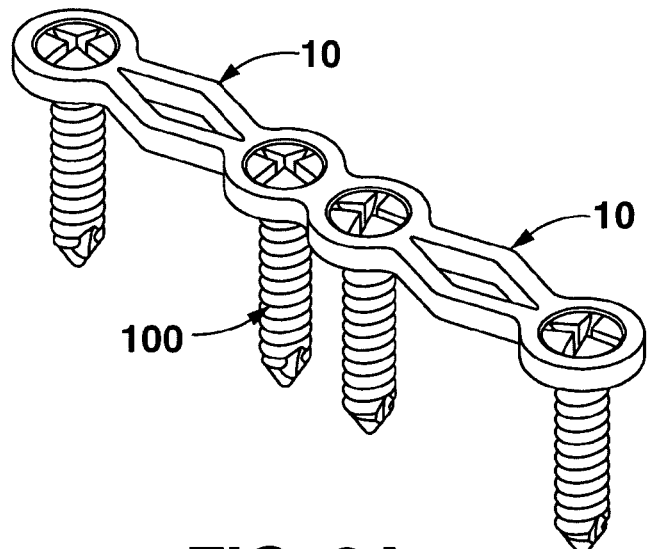
FIGS. 8A-C show views of one preferred embodiment of the invention, featuring a pair of compression brackets joined end-to-end.
Figure 8B:
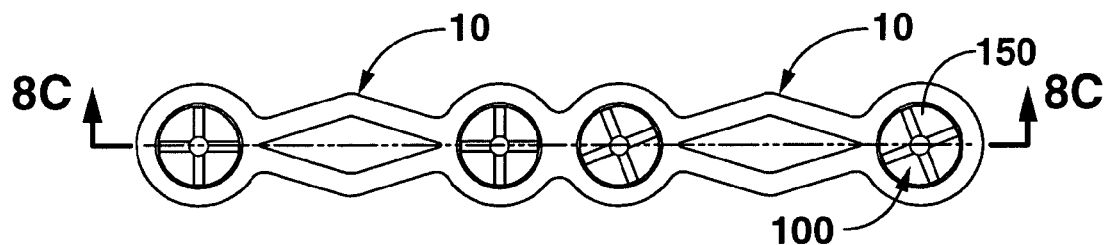
Figure 8C:
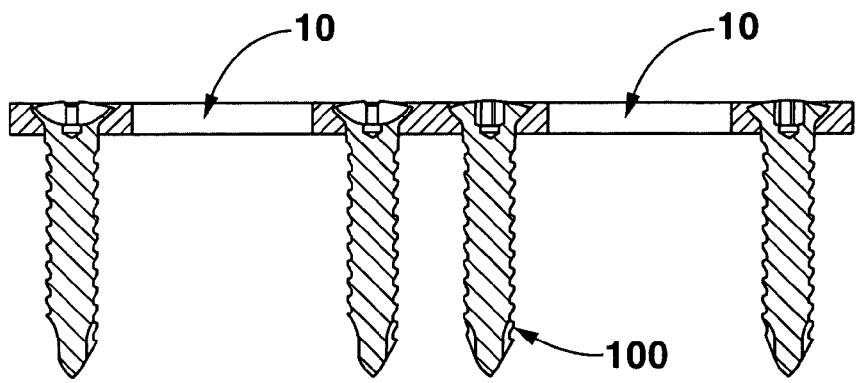
Figure 9A:
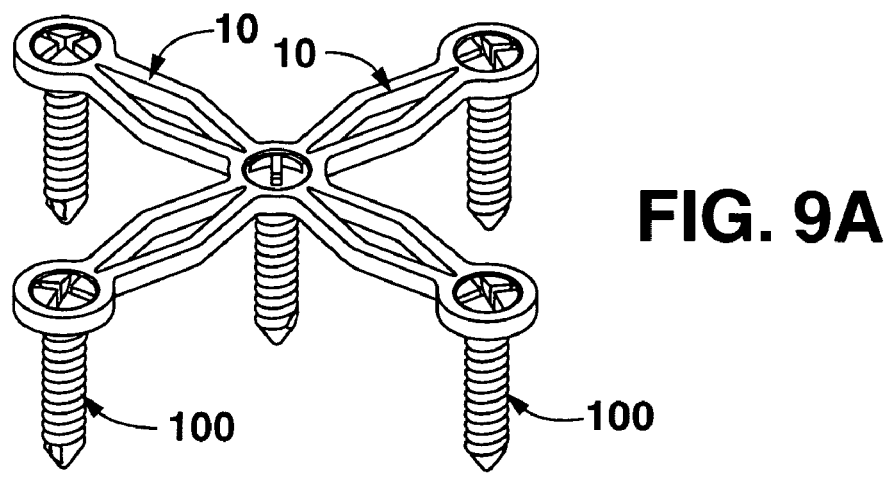
FIG. 9 provides views of one preferred embodiment of the invention, featuring a plurality of clip members radiating from a shared fastener retaining portion.
Figure 9B:
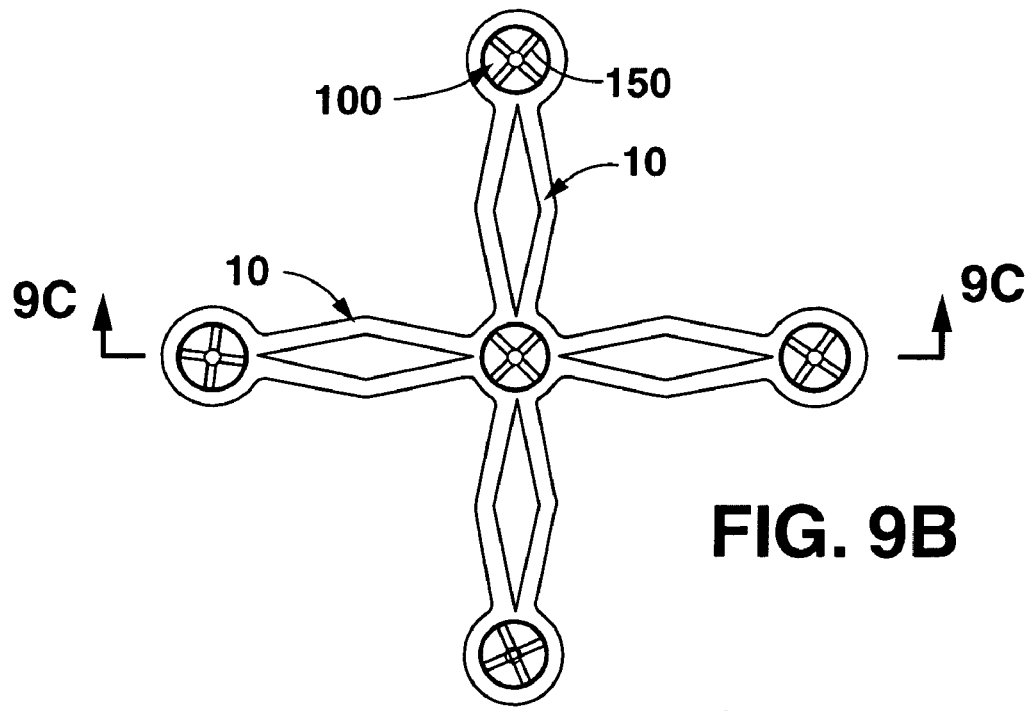
Figure 9C:
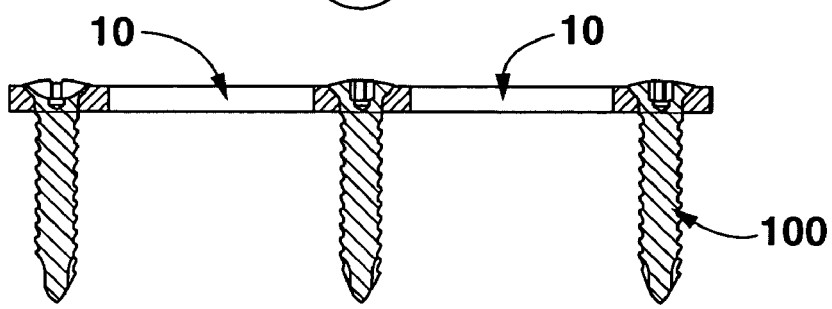
Figure 10A:
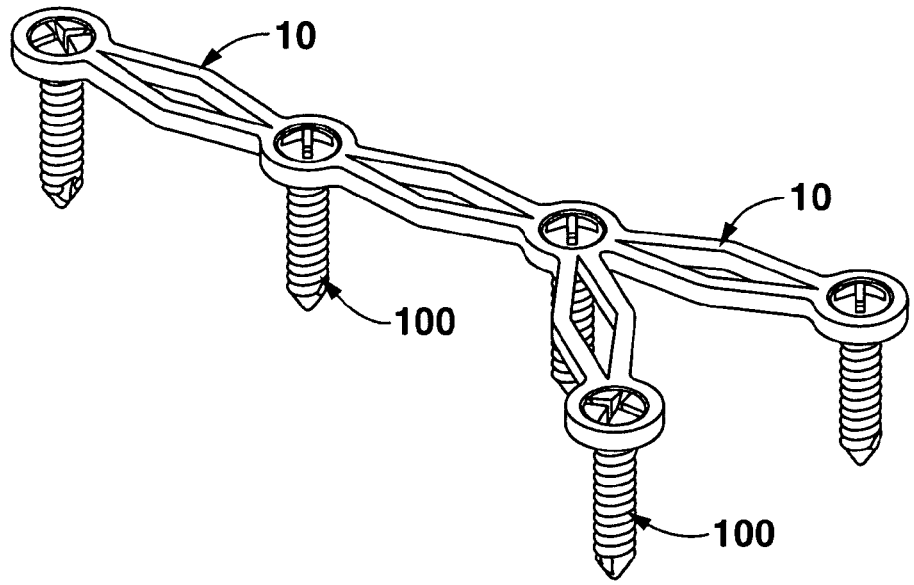
FIG. 10 provides views of one preferred embodiment of the invention, featuring a plurality of compression brackets joined end-to-end via shared fastener retaining portions, and including a branching compression bracket.
Figure 10B:
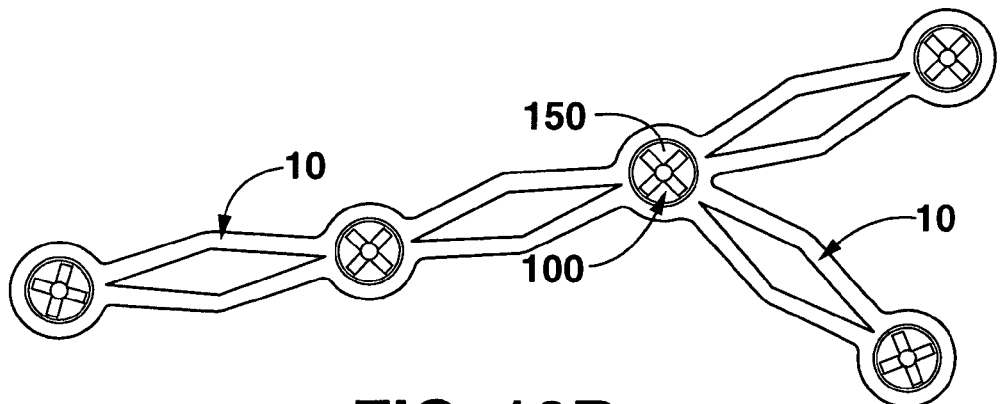
Figure 10C:
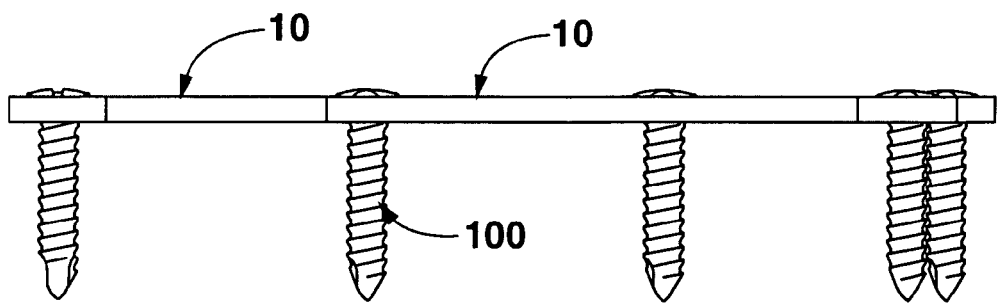

As shown in FIGS. 8-10 and 13, the compression bracket 1 can include a plurality of fastener retaining portions 10 and a plurality of compression openings 70. In the embodiment shown in FIGS. 8A-8C, a pair of compression brackets are joined end-to-end in a unitary or unibody compression bracket structure. FIGS. 13A-C show an end-to-end configuration in which bridge members 50A, 50B are joined by a shared fastener retaining portion 10. In FIGS. 9A-9C, a plurality of bridge members 50A, 50B radiate from a shared fastener retaining portion 10. In FIGS. 10A-10C, a plurality of compression brackets 1 are joined end-to-end via shared fastener retaining portions 10. FIG. 10 also includes a compression bracket that branches off from the main chain via a shared fastener retaining portion 10. Multi-part compression brackets can also be configured to include adjacent compression openings that are not separated by a fastener retaining member 20. Multi-compression brackets such as those shown in FIGS. 8-10 are particularly suited for fixation or distraction of multi-part fractures, such as when a bone fractures into more than two fragments. The multi-compression bracket embodiments shown in FIGS. 8-10 are merely exemplary preferred embodiments of the invention, and are intended to provide those with skill in the art with the building blocks necessary to configure a wide variety of multi-compression bracket configurations, all of which would fall within the scope of the invention.

One of the advantages of the invention over the prior art is that it enables a surgeon to intra-operatively select various combinations of brace and fastener sizes and configurations to accommodate the operative condition of a particular surgical site, thus providing greater options while decreasing staple inventory. To further enhance options, compression braces 1 can be provided with a combination of threaded and unthreaded holes. Such a configuration could be used, for example, in situations where it is desirable to provide a perpendicularly locked fastener on one end of the brace 1, while providing selective angulation of the fastener 100 on the opposing end of the brace. The same effect can be obtained by selecting a fastener 100 sized to permit angulation through a relatively larger threaded hole 20, such that the threads of the hole 20 do not substantially impinge on the selected degree of angulation. Similarly, a combination of locking and non-locking threads can be used.

The compression brace 1 is used primarily for fixation of arthrodeses and osteotomies. The compression brace 1 can also be used in place of conventional plates, such as cuboid plates, hind or mid-foot plates, or calcaneal plates.

Figure 24A:
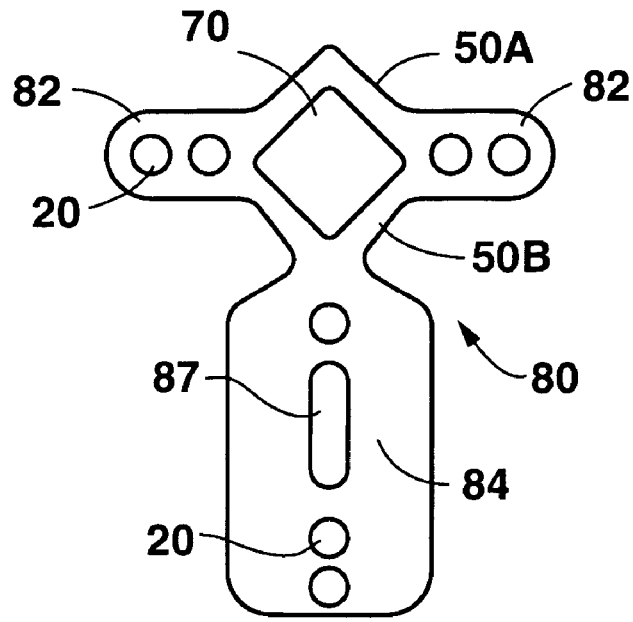
FIG. 24A shows a top view of one preferred embodiment of a fracture fixation plate having a compression opening.

As shown in FIGS. 24-25, the concept of compression braces described herein can be applied to fracture fixation plates, such as plates for fixing fractures of the radius. FIG. 24A shows a fracture fixation plate 80 that has a compression opening 70 along a distal portion of the plate, such as the metaphyseal regions of the plate. The plate 80 has a pair of metaphyseal or distal plate portions 82 disposed along a compression opening 70. The plate 80 of FIG. 24A also includes a diaphyseal or proximal plate portion 84 disposed along a proximal side of the compression opening 70. The plate portions 82, 84 are provided with one or more fastener holes 20 for use in securing the metaphyseal plate portion 82 to a bone of the patient using fasteners, such as the types of fasteners discussed herein. The plates 82, 84 can also be provided with slots 87, which are used in a manner known to those of skill in the art of plate fixation. The distal compression opening 70 can be expanded to draw the distal plate portions 82 toward one another, and thus reduce a fracture. As with the compression braces 1 described herein, the compression openings 70 can be used to selectively expand or compress the openings for fine tuning of the fracture fixation plates 80 and underlying fractures.

Figure 24B:
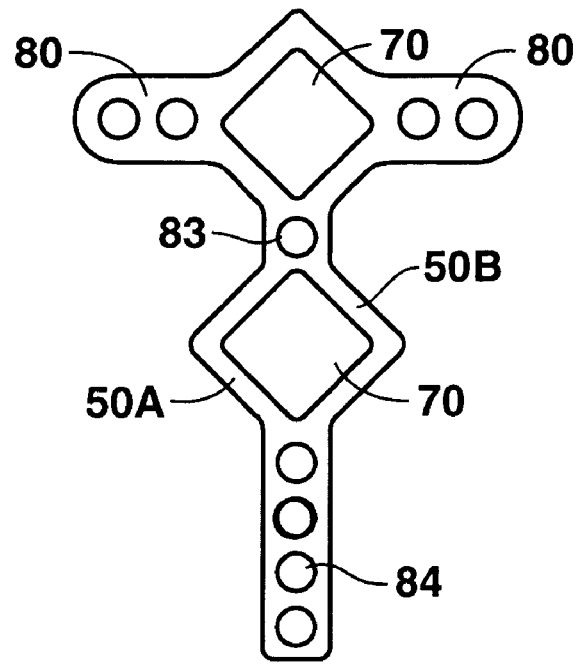
FIG. 24B shows a top view of one preferred embodiment of a fracture fixation plate having a pair of compression openings.

FIG. 24B shows a fracture fixation plate 80 that has a first or distal compression opening 70 along a distal portion of the plate 80, and a second or proximal compression opening 70 located closer to a proximal end of the plate 80, such as in a diaphyseal region of the plate 80. The fracture fixation plate 80 of FIG. 24B includes a proximal plate portion 84 for use in securing a proximal portion of the plate 80 to a bone of the patient. The fracture fixation plate 80 of FIG. 24B also includes an intra-opening plate 83 having at least one fastener hole 20 therethrough. One of the primary advantages of the fracture fixation plate 80 is that the distal compression opening 70 can be expanded to force the proximal plate 84 proximally to thereby extend the fracture, or compressed to reduce the fracture. Additionally, note that the use of a second compression opening 70 makes it possible to eliminate slots 87 from the plate 80 while retaining the capability of expanding a fracture.

FIGS. 25A-25B show the use of a fracture fixation plate 80 to reduce an intra-articular fracture of the distal radius while simultaneously expanding a metaphyseal region to a pre-fracture length. As shown in FIG. 25A-25B, another advantage of the fracture fixation plate 80 is that the compression opening 70 of the compression plate 80 can be used to compress intra-articular fragments of an intra-articular fracture F1 securely against one another, so as to substantially eliminate gaps in the articular surface. Under the prior art, intra-articular fragments had to be manually reduced and then secured together with screws. Additionally, FIG. 25A shows a distal radius fracture in which the injury has resulted in a reduction in the length of the radius along the metaphyseal fracture F2. Expansion of the compression opening 70 pushes the proximal portion 84 of the plate 80 proximally, which restores the length of the metaphysis. The expanded metaphyseal fracture F2 can be filled with an osteoconductive material, such as OSTEOSET® pellets (available from Wright Medical Technology, Inc. of Arlington, Tenn.), to promote healing of the fracture F2 and restoration of normal radius length.

Although FIGS. 24-25 depict a fracture fixation plate 80 that is particularly configured for use as a dorsal or volar fracture fixation plate on the distal radius, the concept of combining compression openings with fracture fixation plates can be applied to virtually any fracture or bone, provided that the compression opening 70 is sufficiently strong to maintain sufficient reduction to allow for healing of the particular fracture. For example, FIG. 26 shows a fracture fixation plate 80 that is configured primarily for use on the diaphysis of long bones. The plate 80 includes a first plate portion 82 and a second plate portion 84, with the plate portions 82, 84 joined together by the opposing bridges 50A, 50B of a compression opening 70.

In operation, the compression brace 1 is used as follows. After preparation of the surgical site, the compression brace 1 is placed on adjacent bones 301, 302 such that one of the fastener holes is on the first bone or bone fragment 301 and one of the fastener holes 302 is on the second bone or bone fragment (see FIG. 4). The first and second bones 301, 302 may of course be fragments or segments of the same bone, i.e. after fracture. The compression brace 1 is secured on the first bone 301 by inserting a fastener 100 through one of the fastener holes 20 and into the first bone 301. The compression brace 1 is secured to the second bone 302 by inserting a fastener 100 through one of the fastener holes 20 and into the second bone. The bridge members 50A, 50B of the compression brace 1 are then spread apart to draw the fasteners 100 and the bones 301, 302 toward one another. During spreading of the bridge members 50A, 50B during compression, sufficient force can be applied to press adjacent bones 301, 302 against one another to substantially eliminate a gap 300 between the bones 301,302. Alternatively, sufficient force can be applied to move the bones 301,302 toward one another a selected distance, but without removing the gap 300. With fractures having more than two bone fragments, more than one compression brace 1 can be used to fix the fracture. Alternatively, a multi-compression bracket such as the embodiments shown in FIGS. 8-10 can be used to fix the various bone fragments. In one embodiment of the method, holes are drilled into the bones 301, 302 through the fastener holes 20, and the fasteners 100 are then installed in the drilled holes. Pre-drilling is unnecessary if self-drilling fasteners 100 are used.

The compression bracket 1 can also be used as a distraction plate, such as for opening osteotomies (e.g. HTO or spine distraction). By applying a force to bridge members 50A, 50B, a space can be created or widened, thus forcing the fasteners 100 apart. The device 1 can be used to open a space to allow insertion of a spacer, and then used to close the space in order to sandwich the spacer between adjacent bones.

Figure 20:
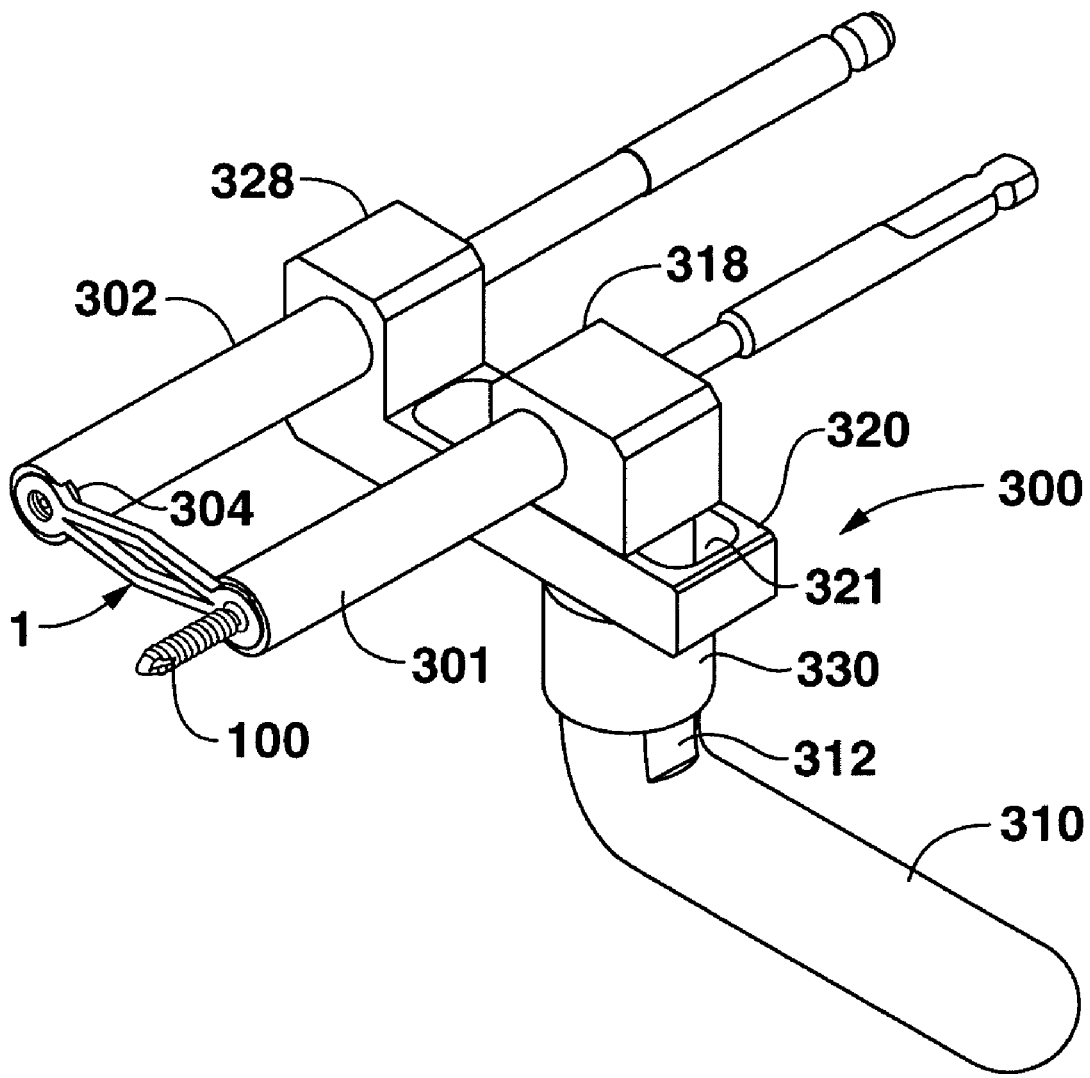
FIG. 20 is a perspective view of one embodiment of a drill guide instrument for use in installing the compression brackets of the invention.

The compression bracket 1 can be installed with or without specialized instrumentation. FIG. 20 shows a preferred drill guide instrument 300 for use in installing the compression braces 1. The drill guide 300 includes a handle or mounting arm 310 having an extension portion 312. A stationary guide base 318 is fixedly mounted on an upper end of the extension portion 312. As shown in FIG. 20, an adjustable guide base 328 is slidably and adjustably engaged to the stationary guide base 318 via an adjustment member 320 having a lengthwise opening 321 therethrough. A locking means 312 is provided for selectively locking the adjustable guide base 328 relative to the stationary guide base 318. In the embodiment shown in FIG. 20, the locking means is a ring 330 threaded on the extension portion 312.

A first drill guide 301 is fixedly mounted on the stationary guide base 318, while a second drill guide 302 is fixedly mounted on the adjustable guide base 328. The drill guides 301, 302 are preferably removable from the drill guide instrument in order to accommodate selected sizes and configurations of fasteners 100 and compression braces 1. A distal end of the drill guide 301, 302 is provided with a counter bore having a side slot 304 therethrough for accommodating a compression brace 1, in the manner shown in FIG. 20.

Figure 21A:
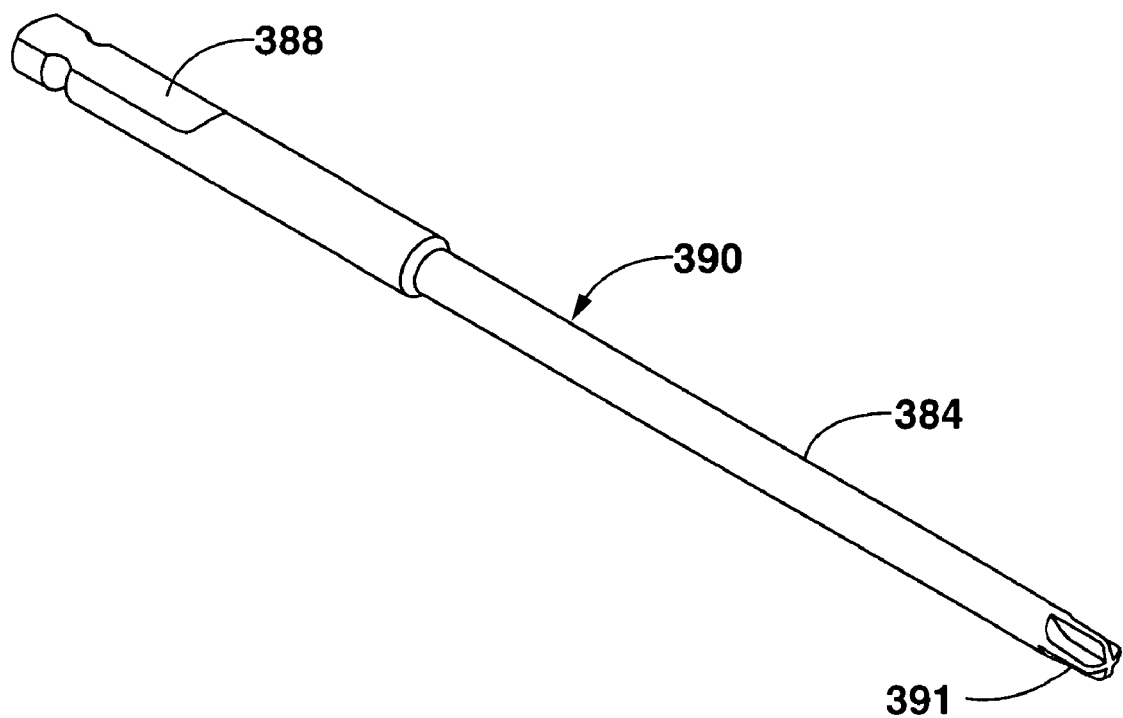
FIG. 21 provides perspective views of drivers for use with the drill guide instrument of FIG. 20.
Figure 21B:
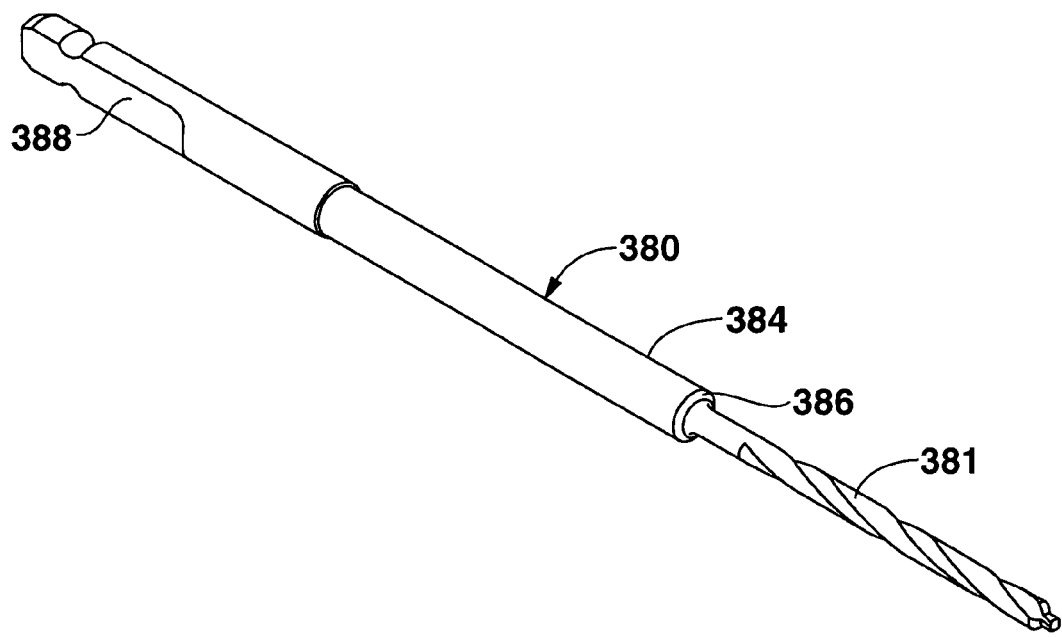

As indicated in FIG. 20, each drill guide 301, 302 has a lengthwise cylindrical sleeve (not shown) passing therethrough. As shown in FIG. 20, the sleeves are sized to receive and provide rotational guidance to driver components such as drill bit 380 (preferred embodiment shown in FIG. 21A) or a screwdriver 390 (preferred embodiment shown in FIG. 21B). As shown in FIGS. 21A and 21B, the driver components 380, 390 have a cylindrical shaft portion 384 sized to permit guided rotation within the drill guides 301,302. A stop 386 is provided on the shaft 384. The stop 386 is sized and positioned to abut against the drill guide 301,302, the guide base 318,328 or another selected portion of the drill guide instrument 300 to prevent over drilling. The drive components 380, 390 are provided with a conventional 388 mount on an upper end for selective engagement with a drive means, in a manner known to those of skill in the art. As shown in FIG. 21A, the drill bit driver component 380 is provided with a drill bit 381. As shown in FIG. 21B, the screw driver component 390 is provided with a screw driver head 391 configured to match the fasteners 100. Various sizes and types of drill bits 381 and screwdrivers 391 can be used with the drill guide instrument 300, depending on intra-operative conditions. A tamping driver (not shown) can be provided for inserting pins 100 with the drill guide instrumentation 300.

As indicated in FIG. 20, the drill guide instrument 300 can be adjusted to the size of a selected compression brace 1 simply by sliding the second drill guide 302 relative to the first drill guide 301 until a suitable position is reached, and then locking the second drill guide 302 in place via the locking means 330. The drill guide instrument 300 aligns the axes of the driver components 380, 390 with those of the fastener holes 20, which enables precise drilling or threading of fastener screws 100.

Spreading of the bridge members 50A, 50B is preferably accomplished using a spreader, such as the type shown in FIG. 10 of U.S. Pat. No. 5,660,188 (Groiso). If crimping of the bridge members 50A, 50B is desired, pliers can be used.

One of the disadvantages of prior art staple spreaders, such as the spreader of U.S. Pat. No. 5,660,188, is that they are designed only for use in spreading the opposing bridges of a compression staple. Prior art spreaders are not designed for holding compression staples, such as during insertion of the staple into predrilled drill holes. Prior art spreaders are also not designed for use in impacting staples into holes. It therefore becomes necessary to use not only a spreader, but also a staple holder and an impactor. There is thus a need for a multi-use spreader that can be used to hold, impact and spread compression braces 1 or compression staples. FIGS. 23A-23E show one preferred embodiment of a multi-use spreader 400 that combines these three functions into a single instrument. As a result, not only are fewer instruments required, but also fewer surgical steps, which allows for simpler and more efficient surgical techniques.

Figure 23A:
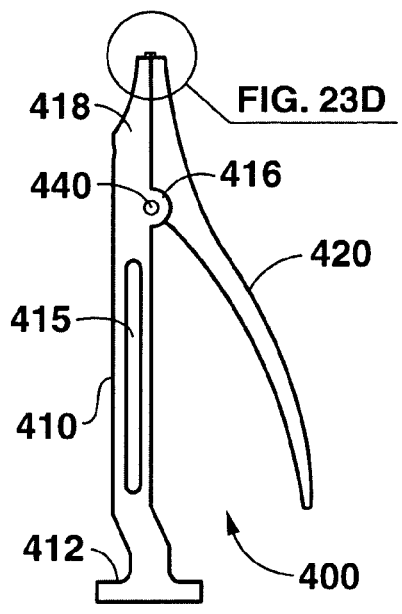
FIG. 23 provides views of a preferred embodiment of a multi-use instrument for holding, impacting and spreading the compression brace of the invention.
Figure 23B:
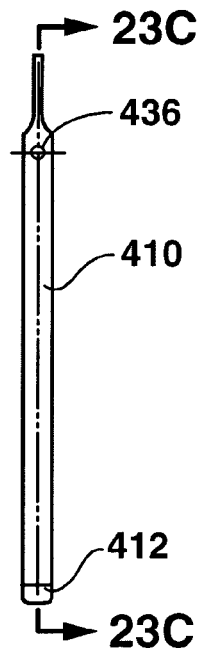

The multi-use spreader 400 shown in FIG. 23A includes, generally, an impactor handle 410 pivotally connected to a spreader handle 420, and a biasing means 430 for normally biasing opposing jaws 418, 428 of the spreader 400 apart from one another. A pair of teeth 418, 428 are formed on distal ends of the jaws 418, 428, and are configured for insertion into the compression opening of a compression member, such as the compression braces 1 described herein or the prior art compression staples. Because the jaws 418, 428 are normally spread apart, the teeth 419, 429 abut against the inner sides of the bridges of the compression opening under tension, and thus serve to hold the compression member on the multi-use spreader 400. With a compression member held firmly by the spreader teeth 419, 429, the multi-use spreader 400 can be used to hold the compression member over a selected spot, such as for inserting fasteners 100 into a compression brace 1 or for inserting the legs of a conventional compression staple into predrilled holes. The multi-use spreader 400 can preferably be readily disassembled for cleaning and repair, and can preferably be autoclaved.

Various features of the impactor handle 410 and spreader handle 420 assist in providing the foregoing functions. A proximal end of the impactor handle 410 is preferably configured for use as an impact surface. As shown in FIG. 23A, an impactor head 412 is preferably formed on the proximal end of the impactor handle 410. The impactor head 412 has a generally mushroom or bulging configuration that provides a platform for use in impacting the impactor handle 410 with a conventional impactor. With a compression member held firmly by the spreader teeth 419, 429, the impactor head 412 can be impacted to drive the spreader teeth into bone, and particularly into pre-drilled holes.

Figure 23C:
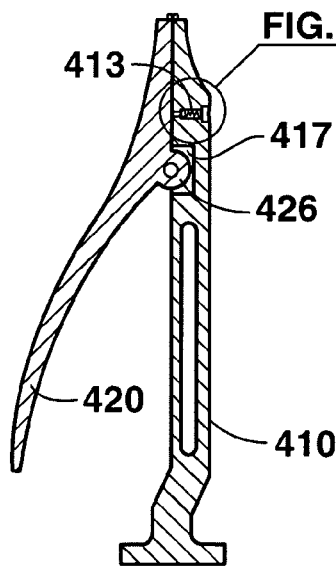

The impactor handle 410 shown in the preferred embodiment of FIG. 23A includes a pivot support 416 extending from the impactor handle 410. As indicated in FIG. 23C, the pivot support 416 is positioned and configured to pivotally engage a pivot support 426 on the spreader handle 420. A pivot means 440, such as a bar 440, provides a hinge-type pivot between the impactor handle 410 and the spreader handle 420. To allow the jaw 428 of the spreader handle 420 to pivot open without impingement by the impactor handle 410, the impactor handle 410 may be provided with a depression or space 417 that is positioned and configured to allow the space 417 to receive a portion of the spreader handle 420.

To assist in providing a means for biasing the jaws 418, 428, the plunger handle 410 maybe provided with a plunger bore 413. In the preferred embodiment shown in FIG. 23C, the plunger bore 413 is located distal to the pivot point 440, in the jaw portion 418 of the impactor handle 410. FIG. 23E provides a cross-section view of a preferred biasing means comprising a spring-biased plunger 430 that is disposed in the plunge bore 413. The spring-biased plunger 430 includes a plunger portion 432, a compression spring 434, and a retainer plug 436. The plunger portion 432 is preferably a round nose ball plunger. As indicated in FIG. 23E, the spring 434 and retainer plug 436 normally bias the plunger 432 in an open position. When in the open position, a tip of the plunger 432 is configured to extend from the plunger bore 413 such that the tip of the plunger 432 impinges on and opens the jaw portion 428 of the spreader handle 420. The plunger 432 includes a shoulder that is configured to abut against a stepdown in the plunger bore 413, and thus to define a maximum biased-open position for the jaws 418,428 while also retaining the plunger 432 in a biased condition in the plunger bore 413. In FIG. 23E, the jaws 418, 428 are shown in a closed position in which that the tip of the plunger 430 has been forced into the plunger bore 413 by the inner surface of the jaw 428 of the spreader handle 420. By drawing the handles 410, 420 toward one another, the jaws 418, 428 can be spread apart to deform the bridges of a compression member.

As shown in FIG. 23A, the impactor handle 410 is preferably provided with a lengthwise slot 415. The impactor slot 415 serves to lighten the spreader 400, and can be configured to redistribute the center of gravity, such as to make the device head light. The impactor slot 415 can also serve as finger hold for the surgeon, which assists in preventing the instrument from slipping in the hands of the surgeon, who may be holding the device with wet surgical gloves. These features make it easier to maneuver and position the instrument 400 during surgery.

Figure 23D:
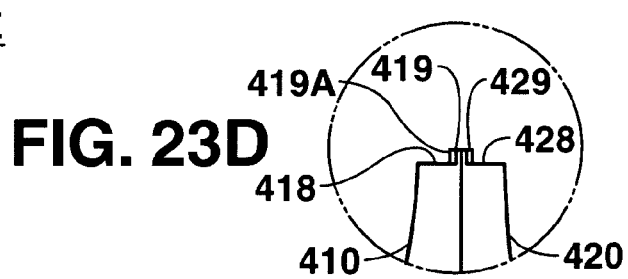
Figure 23E:
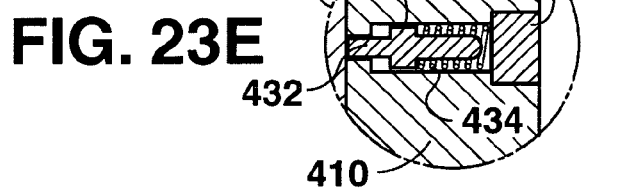
Figure 23F:
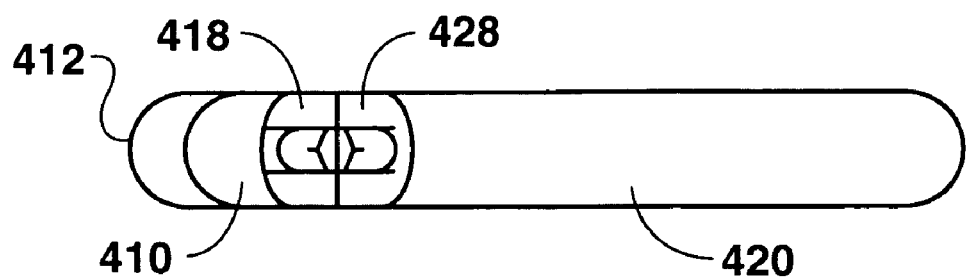
Figure 23G:
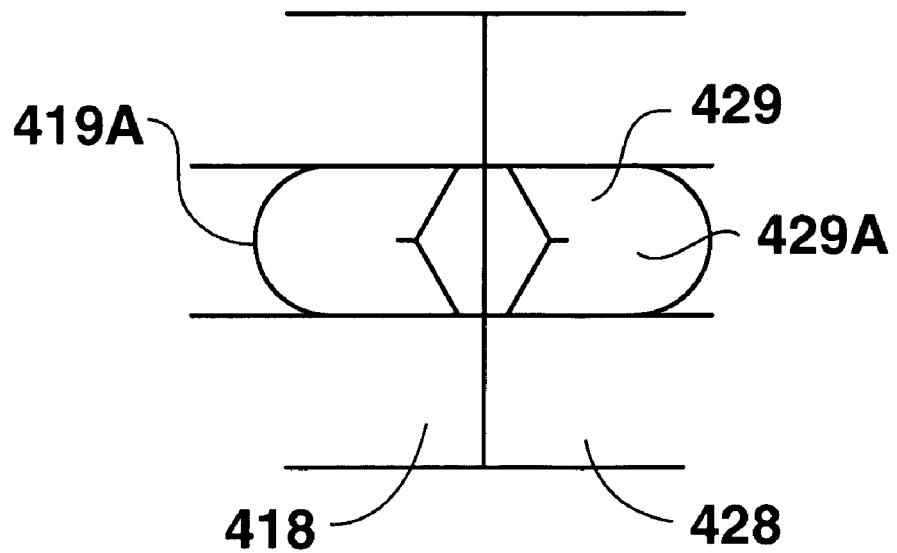

Details of a preferred configuration of the teeth 419,429 are shown in FIGS. 23D, 23F, and 23G. As indicated in FIG. 23D, the distal ends of each of the jaw portions 418,428 are preferably provided with a generally flattened impact shoulder 418A, 428A. The opposing impact shoulders 418A, 428A provide a surface for retaining and supporting compression members of various sizes during holding, and for driving compression members of various sizes during impaction. As shown in FIG. 23D each jaw 418, 428 is provided with a tooth member, which can be referred to as an impactor tooth 419 and a spreader tooth 429, respectively. As shown in FIG. 23D, the teeth 419, 429 are preferably positioned on an inner side of the respective jaws 419, 429 so as to abut or nearly abut against one another when the instrument is in a closed configuration. Each tooth 419, 429 is configured to hold the opposing bridges of a compression member. As indicated in the top views of FIGS. 23F-23G, the teeth 419, 429 are preferably relatively narrow so as to enable the teeth 419, 429 to engage and spread a plurality of sizes of compression members. As indicated most clearly in FIG. 23G, each tooth 419, 429 may be configured to include a bridge engaging portion 419A, 429A which generally extends outward in a curved or curvilinear fashion to accommodate the bend in the bridges of compression members.

The device and method can be used to join, fix and maintain bones in various procedures, including: LisFranc arthrodesis; mono or bi-cortical osteotomies in the forefoot; first metatarsophalangeal arthrodesis; Akin osteotomy; midfoot and hindfoot arthrodeses or osteotomies; fixation of osteotomies for hallux valgus treatment (Scarf and Chevron); and arthrodeses of the metatarsocuneiform joint to reposition and stabilize the metatarsus primus varus; carpal bone fusion; wrist fusion; elbow fracture; and metacarpal fractures.

The compression brace 1 and fasteners 100 are preferably made of suitable biocompatible materials having sufficient mechanical strength and elasticity for the desired applications of the invention 1. Suitable materials include medical grade titanium alloys, medical grade stainless steel, and cobalt chrome. A memory metal, such as nitinol, can be incorporated into the invention. Suitable non-metallic biocompatible materials can also be used. Further, the brace 1 or fasteners 100 can be made of a suitable bio-absorbable material, such that the components are eventually absorbed by the body after healing of the bone parts.

Unless the context indicates otherwise, the term "bone" as used herein includes whole bones as well as bone fragments (i.e. the two or more fragments of a particular bone that remain after the bone has been fractured, either completely or incompletely).

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A snap-off surgical screw configured for threading into a bone of a patient using a driver member, comprising:
    a shaft extension joined to a screw portion via a frangible connection, said frangible connection comprising at least one defect formed through an outer surface of said frangible connection, and said defect configured to promote selective separation of said shaft extension from said screw portion at said defect,
    a proximal end of said screw portion having a recess formed in said proximal end thereof, said recess being in the form of a distally recessed well having a sidewall spaced from said frangible connection, said frangible connection positioned in said recess to thereby configure said shaft extension to snap-off from said screw portion below said proximal end of said screw portion,
    said shaft extension including a driver engaging portion, said driver engaging portion comprising an enlarged portion adjacent and proximal to said proximal end of said screw portion, said enlarged portion including a plurality of slots therein, each of said slots extending from a proximal end to a distal end of said enlarged portion to thereby form a through slot, and said slots configured for engagement by a driver member.

2. The snap-off surgical screw of claim 1, wherein said enlarged portion has three of said slots.

3. The snap-off surgical screw of claim 1, wherein each of said slots include a tapered wall on an inner center wall thereof.

4. The snap-off surgical screw of claim 1, wherein said driver engaging portion includes a quick connect means for quickly connecting the screw to a quick connect coupling member.

5. The snap-off surgical screw of claim 4, wherein said driver engaging portion includes a non-circumferential portion configured to engage the driver member in a non-rotational relationship.

6. The snap-off surgical screw of claim 1, wherein said defect comprises a substantially circumferential groove.

7. The snap-off surgical screw of claim 1, wherein said defect comprises at least one substantially wedge shaped opening.

8. The snap-off surgical screw of claim 1, wherein said sidewall of said recess is a continuous sidewall axially spaced from said frangible connection.

9. The snap-off surgical screw of claim 8, wherein said shaft extension includes a straight, untapered length-wise rod portion extending proximally from said driver engaging portion, said rod portion axially aligned with said screw portion, and said rod portion having a substantially narrower width than said driver engaging portion.

10. A snap-off surgical screw configured for threading into a bone of a patient using a driver member, comprising:
    a shaft extension joined to a screw portion via a frangible connection, said screw portion having a head on a proximal end thereof, said shaft extension having a driver engaging portion, the frangible connection formed in a recess in a proximal end of said head, said recess being in the form of a distally recessed well having a sidewall spaced from said frangible connection, said frangible connection comprising at least one defect, and said defect configured to promote selective separation of said driver shaft extension from said screw portion below said proximal end of said head of said screw portion,
    said driver engaging portion comprising an enlarged portion of said shaft extension, said enlarged portion adjacent and proximal to a proximal end of said screw portion, said enlarged portion including a plurality of slots therein, said slots formed along an outer surface of said enlarged portion of said shaft extension, each of said slots having an open outer side, each of said slots extending from a proximal end to a distal end of said enlarged portion to thereby form a through slot, said slots configured for engagement by a driver member, and said head of said screw comprising an enlarged driver head having slots, said slots comprising open slots formed along an outer surface of said enlarged driver head.

11. The snap-off surgical screw of claim 10, wherein each of said slots includes a tapered wall on an inner center wall thereof.

12. The snap-off surgical screw of claim 11, wherein said defect comprises a substantially circumferential groove.

13. The snap-off surgical screw of claim 11, wherein said defect comprises at least one substantially wedge shaped opening.

14. The snap-off surgical screw of claim 10, wherein said driver engaging portion includes a quick connect means for quickly connecting the screw to a quick connect coupling member.

15. The snap-off surgical screw of claim 14, wherein said driver engaging portion includes a non-circumferential portion configured to engage the driver member in a non-rotational relationship.

16. The snap-off surgical screw of claim 10, wherein said defect comprises a substantially circumferential groove.

17. The snap-off surgical screw of claim 10, wherein said defect comprises at least one substantially wedge shaped opening.

18. The snap-off surgical screw of claim 10, wherein said enlarged portion has three of said slots.

19. The snap-off surgical screw of claim 10, wherein each of said slots extends from a proximal end to a distal end of said enlarged portion to thereby form a through slot.

20. The snap-off surgical screw of claim 10, wherein said sidewall of said recess is a continuous sidewall axially spaced from said frangible connection.

21. The snap-off surgical screw of claim 20, wherein said shaft extension includes a straight, untapered length-wise rod portion extending proximally from said driver engaging portion, said rod portion axially aligned with said screw portion, and said rod portion having a substantially narrower width than said driver engaging portion.

* * * * *